(12) United States Patent
Ho et al.

(10) Patent No.: US 7,527,927 B1
(45) Date of Patent: May 5, 2009

(54) STABLE RECOMBINANT YEASTS FOR FERMENTING XYLOSE TO ETHANOL

(75) Inventors: Nancy W. Y. Ho, West Lafayette, IN (US); Zheng-Dao Chen, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1610 days.

(21) Appl. No.: 09/180,340

(22) PCT Filed: May 6, 1997

(86) PCT No.: PCT/US97/07663

§ 371 (c)(1),
(2), (4) Date: Aug. 20, 1999

(87) PCT Pub. No.: WO97/42307

PCT Pub. Date: Nov. 13, 1997

Related U.S. Application Data

(60) Provisional application No. 60/016,865, filed on May 6, 1996.

(51) Int. Cl.
*C12Q 1/68* (2006.01)
(52) U.S. Cl. .................. 435/6; 435/7.1; 435/320.1; 435/325; 435/69.1
(58) Field of Classification Search ............... 435/158, 435/252.3, 139, 169, 105, 161, 320.1, 163, 435/172.3, 183, 325, 254.21, 69.1; 530/380, 530/350; 536/23.5, 23.7, 23.1
See application file for complete search history.

(56) References Cited

U.S. PATENT DOCUMENTS 5,789,210 A * 8/1998 Ho et al. .................. 435/163
5,866,382 A * 2/1999 Hallborn et al. ............ 435/158

FOREIGN PATENT DOCUMENTS

| CA | 2090122 | 6/2002 |
|---|---|---|
| EP | 0450430 A2 | 10/1991 |
| EP | 0450430 A3 | 10/1991 |
| EP | 0450430 B1 | 10/1991 |
| EP | 0 450 430 B1 | 6/1997 |
| WO | WO 91/15588 | 10/1991 |
| WO | WO 95/13362 | 5/1995 |

OTHER PUBLICATIONS

Ammerer, G., "Expression Of Genes In Yeast Using The *ADC1* Promoter," *Methods In Enzymology*, vol. 101, pp. 192-201 (1983).

Amore, R., Wilhelm, M. and Hollenber, C.P., "The Fermentation Of Xylose—An Analysis Of The Expression Of *Bacillus* And *Actinoplanes* Xylose Isomerase Genes In Yeast," *Appl. Microgiol. Biotechnol.*, vol. 30, pp. 351-357 (1989).

Becker, D.M. and Guarente, L., "High-Efficiency Transformation Of Yeast By Electroporation," *Methods In Enzymology*, vol. 194, pp. 182-187 (1991).

Bennetzen, J.L. and Hall, B.D., "The Primary Structure Of The *Saccharomyces cerevisiae* Gene For Alcohol Dehydrogenase I," *J. Biol. Chem.*, vol. 257, No. 6, pp. 3018-3025 (1982).

Burke, R.L., Tekamp-Olson, P. and Najarian, R., "The Isolation, Characterization, And Sequence Of The Pyruvate Kinase Gene Of *Saccharomyces cerevisiae*," *J. Biol. Chem.*, vol. 258, No. 4, pp. 2193-2201 (1983).

Chang, S-F. and Ho, N.W.Y., "Cloning The Yeast Xylulokinase Gene For The Improvement Of Xylose Fermentation," pp. 313-318 (1988).

Chen, Z. and Ho, N.W.Y., "Cloning And Improving The Expression Of *Pichia stipitis* Xylose Reductase Gene In *Saccharomyces cerevisiae*," *Appl. Biochem. And Biotech.*, vol. 39, No. 40, pp. 135-147 (1993).

Chevallier, M.R. and Aigle, M., "Qualitative Detection Of Penicillinase Produced By Yeast Strains Carrying Chimeric Yeast-Coli Plasmids," *FEBS Letters*, vol. 108, No. 1, pp. 179-180 (Dec. 1979).

Chiang, L-C., Hsiao, H-Y., Ueng, P.P., Chen, L-F. and Tsao, G.T., "Ethanol Production From Xylose By Enzymic Isomerization And Yeast Fermentation," pp. 263-274.

D'Amore, T., Celotto, G., Russell, I. and Stewart, G.G., "Selection And Optimization Of Yeast Suitable For Ethanol Production At 40° C.," *Enzyme Microb. Technol.*, vol. 11, pp. 411-416 (Jul. 1989).

(Continued)

*Primary Examiner*—Hope A Robinson
(74) *Attorney, Agent, or Firm*—Mueting Raasch & Gebhardt, P.A.

(57) ABSTRACT

Described are recombinant yeast which ferment xylose to ethanol and which maintain their ability to do so when cultured for numerous generations in non-selective media. The preferred yeast contain multiple copies of integrated genes encoding xylose reductase, xylitol dehydrogenase, and xylulokinase fused to promoters which are non-glucose inhibited and which do not require xylose for induction. Also described are preferred methods for integrating multiple copies of exogenous DNA into host cells by transforming cells with replicative/integrative vectors, and then replicating the cells a number of times under selective pressure to promote retention of the vector in subsequent generations. The replicated vectors thus serve to integrate multiple copies of the exogenous DNA into the host cells throughout the replication/selection phase. Thereafter the selective pressure can be removed to promote loss of the vector in subsequent generations, leaving stable integrants of the exogenous DNA.

3 Claims, 12 Drawing Sheets

OTHER PUBLICATIONS

D'Amore, T., Panchal, C.J., Russell, I., Stewart, G.G., "A Study Of Ethanol Tolerance In Yeast," *Critical Reviews In Biotechnology*, vol. 9, No. 4, pp. 287-304 (1990).

Deng, X.X. and Ho, N.W.Y., "Xylulokinase Activity In Various Yeasts Including *Saccharomyces cerevisiae* Containing The Cloned Xylulokinase Gene," *Appl. Biochem. And Biotech.*, vol. 24, No. 25, pp. 193-199 (1990).

Fujii, T., Kondo, K., Shimizu, F., Sone, K'K., Tanaka, J-I. and Inoue, T., "Application Of A Ribosomal DNA Integration Vector In The Construction Of A Brewer's Yeast Having α-Acetolactate Decarboxylase Activity," *Appl. Environ. Microbiol.*, vol. 56, No. 4, pp. 997-1003 (Apr. 1990).

Grootjen, D.R.J., van der Lans, R.G.J.M. and Luyben, K.Ch.A.M., "Effects Of The Aeration Rate On The Fermentation Of Glucose And Xylose By *Pichia stipitis* CBS 5773," *Enzyme Microb. Technol.*, vol. 12, pp. 20-23 (Jan. 1990).

Hallborn, J., Walfridsson, M., Airaksinen, U., Ojamo, H., Hahn-Hägerdal, B., Penttilä, M. and Keränan, S., "Xylitol Production By Recombinant *Saccharomyces cerevisiae*," *Biotechnology*, vol. 9, pp. 1090-1095 (Nov. 1991).

Ho, N.W.Y. and Chang, S-F., "Cloning Of Yeast Xylulokinase Gene By Complementation Of *E. coli* And Yeast Mutations," *Enzyme Microb. Technol.*, vol. 11, pp. 417-421 (Jul. 1989).

Ho, N.W.Y., Stevis, P., Rosenfeld, S., Huang, J.J. and Tsao, G.T., "Expression Of The *E. coli* Xylose Isomerase Gene By A Yeast Promoter," *Biotech. And Bioeng. Symp. No. 13*, pp. 245-250 (1983).

Holland, J.P. and Holland, M.J., "The Primary Structure Of A Glyceraldehyde-3-Phosphate Dehydrogenase Gene From *Saccharomyces cerevisiae*," *J. Biol. Chem.*, pp. 9839-9845 (1979).

Jeffries, T.W., "Emerging Technology For Fermenting D-xylose," pp. 208-212.

Jeffries, T.W., "Utliization Of Xylose By Bacteria, Yeasts, And Fungi," pp. 1-32.

Kötter, P., Amore, R., Hollenberg, C.P. and Ciriacy, M., "Isolation And Characterization Of The *Pichia stipitis* Xylitol Dehydrogenase Gene, XYL2, And Construction Of A Xylose-Utilizing *Saccharomyces cerevisiae* Transformant," *Curr. Genet.*, vol. 18, pp. 493-500 (1990).

Kötter, P. and Ciriacy, M., "Xylose Fermentation By *Saccharomyces cerevisiae*," *Appl. Microbiol. Biotechnol.*, vol. 38, pp. 776-783 (1993).

Kunkel, T.A., Roberts, J.D. and Zakour, R.A., "Rapid And Efficient Site-Specific Mutagenesis Without Phenotypic Selection," *Meth. Enzymol.*, vol. 154, p. 367-382 (1987).

Lastick, S.M., Tucker, M.Y., Beyette, J.R., Noll, G.R. and Grohmann, K., "Simultaneous Fermentation And Isomerization Of Xylose," *Appl. Microbiol. Biotechnol.*, vol. 30, pp. 574-579 (1989).

Le Dall, M-T., Nicaud, J-M. and Gaillardin, C., "Multiple-Copy Integration In The Yeast *Yarrowia lipolytica*," *Curr. Genet.*, vol. 26, pp. 38-44 (1994).

Lopes, De Wijs, I.J., Steenhauer, S.I., Verbakel, J. and Plants, R.J., "Factors Affecting The Mitotic Stability Of High-Copy-Number Integration Into The Ribosomal DNA Of *Saccharomyces cerevisiae*," vol. 12, pp. 467-477 (1996).

Rosenfeld, S.A., Stevis, P.E. and Ho, N.W.Y., "Cloning And Characterization Of The *xyl* Genes From *Escherichia coli*," *Mol. Gen. Genet.*, vol. 194, pp. 410-415 (1984).

Sarthy, A.V., McConaughy, B.L., Lobo, Z., Sundstrom, J.A., Furlong, C.E. and Hall, B.D., "Expression Of The *Escherichia coli* Xylose Isomerase Gene In *Saccharomyces cerevisiae*," *Appl. Environ. Microbiol.*, vol. 53, No. 9, pp. 1996-2000 (Sep. 1987).

Stevis, P.E. and Ho, N.W.Y., "Overproduction Of D-xylose Isomerase In *Escherichia coli* By Cloning The D-xylose Isomerase Gene," *Enzyme Microb. Technol.*, vol. 7, pp. 592-596 (Dec. 1985).

Stevis, P.E., Huang, J.J. and Ho, N.W.Y., "Cloning Of The *Pachysolen tannophilus* Xylulokinase Gene By Complementation In *Escherichia coli*," *Appl. Environ. Microbiol.*, vol. 53, pp. 2975-2977 (Dec. 1987).

Takuma, S., Nakashima, N., Tantirungkij, M., Kinoshita, S., Okada, H., Seki, T. and Yoshida, T., "Isolation Of Xylose Reductase Gene Of *Pichia stipitis* And Its Expression In *Saccharomyces cerevisiae*," *Appl. Biochem. Biotechnol.*, vol. 28, No. 29, pp. 327-340 (1991).

Tantirungkij, M., Izuishi, T., Seki, T. and Yoshida, T., Fed-Batch Fermentation Of Xylose By A Fast-Growing Mutant Of Xylose-Assimilating Recombinant *Saccharomyces cerevisiae*, *Appl. Microbiol. Biotechnol.*, vol. 41, pp. 8-12 (1994).

Tantirungkij, M., Seki, T. and Yoshida, T., "Genetic Improvement Of *Saccharomyces cerevisiae* For Ethanol Production From Xylose," *Ann. N.Y. Acad. Sci.*, pp. 138-147 (May 2, 1994).

Toivola, A., Yarrow, D., van den Bosch, E., van Dijken, J.P. and Scheffers, W.A., "Alcoholic Fermentation of d-Xylose By Yeasts," *Appl. Environ. Microbiol.*, vol. 47, No. 6, pp. 1221-1223 (Jun. 1984).

Wilhelm, M. and Hollenberg, C.P., "Selective Cloning Of *Bacillus subtilis* Xylose Isomerase And Xylulokinase In *Escherichia coli* Genes by IS5-Mediated Expression," *EMBO J.*, vol. 3, No. 11, pp. 2555-2560 (1984).

Yamano, S., Kondo, K., Tanaka, J. and Inoue, T., "Construction Of A Brewer's Yeast Having α-Acetolactate Decarboxylase Gene From *Acetobacter aceti* ssp. *Xylinum* Integrated In The Genome," *J. Biotech.*, vol. 32, pp. 173-178 (1994).

Zalkin, H. and Yanofsky, C., "Yeast Gene TRP5: Structure, Function, Regulation," *J. Biol. Chem.*, vol. 257, No. 3, pp. 1491-1500 (1982).

Ho, N., et al., *Engineering or Xylose Metabolic Pathway in Saccharomyces cerevisiae*, Faseb J. 5(6):Abstract 6608 (Mar. 19, 1991).

Lachke, A. and Jeffries, T., *Levels of Enzymes of the Pentose Phosphate Pathway in Pachysolen tannophilus Y-2460 and Selected Mutants*, Enzyme Microb. Technol., 8:353-359 (1986).

Batt et al. "Direct Evidence for a Xylose Metabolic Pathway in *Saccharomyces cerevisiae*" Biotechnology and Bioengineering 1986;28:549-553.

Bruinenberg et al. "NADH-linked aldose reductase: the key to anaerobic alcoholic fermentation of xylose by yeasts" *Appl. Micrbio Biotechno.* 1984;19:256-260.

Chan et al. "Autonomously Replicating Sequences in *Saccharomyces cerevisae*," Proc. Natl. Acad. Sci., 1980;77(11):6329-6333.

Chiang et al. "Ethanol Production form Xylose by Enzymic Isometerization and Yeast Fermentation," *Biotechnol Bioeng. Symp. No. 11*, 1981;263-274.

Clayton et al. "Direct inhibition of testicular function by gonadotropin-releasing hormone: mediation by specific gonadotripin-releasing hormone receptors in interstitial cells," *Proc. Natl. Acad. Sci. USA*, 1980;77(8):4450-4463.

Cregg et al. "*Pichia pastoris* as a Host System for Transformation," *Molecular and Cellular Biology* 5:3376-3385.

duPreez et al. "Fermentation of D-xylose to ethanol by a strain by *Candida schehatae*" Biotechnol. Lett. 1983;5(5):357-362.

Gietz et al. "Genetic Transformation of Yeast," *BioTechniques*, 2001;30(4):816-831.

Grootjen et al. "Effects of the aeration rate on the fermentation of glucose and xylose by *Pichia stipitis* CBS 5773" *Enzyme Microb. Technol.* 1990;12:20-23.

Ho et al. "Development of a cloning system for *Candida* species" *Biotechnol. Bioengineering Symp. No. 14* 1984:295-301.

Ho et al. "Genetically Engineered *Saccharomyces* Yeast Capable of Effective Cofermentation of Glucose and Xylose," *Applied and Environmental Microbiology*, 1998; 64(5):1852-1859.

Ho et al. "Genetically Engineered *Saccharomyces* Yeast for Conversion of Cellulosic Biomass to Environmentally Friendly Transportation Fuel Ethanol," American Chemical Society Symposium Series 767 (2000).

Ho et al. "Site-directed mutagenesis by overlap extension using the polymerase chain reaction," *Gene* 1989;77:51.

Jeffries "Emerging Technology for Fermenting D-xylose: Trends in Biotechnology" 1985;3(8):208-212.

Jeffries, "Utilization of xylose by bacteria, yeasts, and fungi," *Adv. In Bioch Engr. Biotechnol.* 1983;27:1-32.

Kotter et al. "Isolation and characterization of the *Pichia stipitis* xylitol dehydrogenase gene, XYL2, and construction of a xylose-utilizing *Saccharomyces cerevisiae* transformant." *Curr Genet*. Dec. 1990;18(6):493-500.

Kotter et al. "Xylose Fermentation by *Saccharomyces cerevisiae*," *Appl. Microbiol. Biotechnol*, 1993;38:776-783.

Kudla et al. "A multisite integrative cassette for the yeast *Saccharomyces cerevisae*," *Gene*; 119:49-56.

Kunkel. "Rapid and efficient site-specific mutagenesis without phenotypic selection" *Proc. Natl. Acad. Sci. USA*, 1985;82:488-492.

Kurtz et al. "Integrated Transformation of *Candida albicans*, Using a Cloned *Candida* ADE2 Gene," *Molecular and Cellular Biology*, 1986;6(1):142-149.

Lopes et al. "High-copy-number integration into the ribosomal DNA of *Saccharomyces cerevisiae*: a new vector for high-level expression," *Gene*, 1989;79(2):199-206.

Lopes et al. "Mechanism of high-copy-number integration of pMIRY-type vectors into the ribosomal DNA of *Saccharomyces cerevisiae*" *Gene*, 105(1);1991:83-90.

Moerschell et al. "Transformation of Yeast with Synthetic Oligonucleotides," *Proc. Natl. Acad. Sci.*, 1988;85:524,528.

Orr-Weaver et al. "Yeast Transformation: A Model System for the Study of Recombinatoin," *Proc. Natl. Acad. Sci.*, 1981:78(10): 6354-6358.

Orr-Weaver et al. "Multiple, Tandem Plasmid Integration in *Saccharomyces cerevisiae*," *Molecular and Cellular Biology* 1983;3(4):747-749.

Rine et al. "Targeted selection of recombinant clones through gene dosage effects." Proceedings of the National Academy of Sciences, USA. Nov. 1983;80:6750-6754.

Romanos et al. "Foreign Gene Expression in Yeast: a Review" *Yeast*, 1992;8(6):423-488.

Rossolini et al. "Kluyvermyces lactis rDNA as a target for multiple integration by homologous recombination," *Elsevier Science Publishers* 1992;75-81.

Rothstein et al. "One-Step Gene Disruption in Yeast," *Methods in Enzymology*, 1981;101:202-211.

Rothstein et al. "Targeting, Disruption, Replacement, and Allele Rescue: Integrative DNA Transformation in Yeast," *Methods in Enzymology*, 1991;194:281-301.

Sakai et al. "Integration of heterologous genes into the chromosome of *Saccharomyces cerevisiae* using a delta sequence of yeast retrotransposen Ty," *Appl. Microbiol. Biotechnol.*, 1990;33:302-306.

Sakai et al. "Enhanced Secretion of Human Nerve Growth Factor from *Saccharomyces cerevisiae* Using an Advanced d-Integration System," *Bio/Technology*, 1991;9:1382-1385.

Sambrook et al. "Molecular Cloning," published by Cold Spring Harbor Lab. Press. 1989;4.10-4.11.

Stevis et al. "Cloning of the *Pachysolen tannophilus* Xylulokinase Gene by complementation in *Escherichia coli*," *Appl. Envion. Microbiol* 1987;53(2975-2977).

Stinchcomb et al. "Eukaryotic DNA segments capable of autonomous replication in yeast," *Proc. Natl. Acad. Sci.* 1980;77(8):4559-4563.

Struhl et al. "High-frequency transformation of yeast: Autonomous replication of hybrid DNA molecules," *Proc. Natl. Acad. Sci.* 1979;76(3):1035-1039.

Szostak et al. "Insertion of a Genetic Market into the Ribosomal DNA of Yeast," *Plasmid* 1979;2:536-554.

Takuma et al. "Isolation of xylose reductase gene of *Pichia stipitis* and its expression in *Saccharomyces cerevisiae*." *Appl Biochem Biotechnol.* 1991;Spring;28-29:327-40.

Tantirungkij et al. "Construction of Xylose-Assimilating *Saccharomyces cerevisiae*," Journal of Fermentation and Bioengineering, 1993;75(2):83-88.

Toon et al. "Enhanced Coferementation of Glucose and Xylose by Recombinant *Saccharomyces* Yeast Strains in Batch and Continuous Operating Modes," Applied Biochemistry and Biotechnology, 63-65;1997:243-255.

Valenzuela et al. "Ribosomal RNA genes of *Saccharomyces cerevisiae* II. Physical map and nucleotide sequence of the 5 S ribosomal RNA gene and adjacent intergenic Region" *The Journal of Biological Chemistry*, 1977;252(22):8126-8135.

Walfridsson et al. "Expression of different levels of enzymes from the *Pichia stipitis XYL1* and *XYL2* genes in *Saccharomyces cerevisiae* and its effects on product formation during xylose utilisation" *Appl Microbiol Biotechnol* 1997;48:218-224.

Ward. "Single-step purification of shuttle vectors from yeast for high frequency back-transformation into *E. coli*" *Nucleic Acids Research*, 1990;18:5319.

Faber et al. "Chromosomal targeting of replicating plasmids in the yeast *Hansenula polymorpha*" *J of General Microbiology* 1992;138:2405-15.

Cannon et al., "Cloning and expression of *Candida albicans ADE2* and proteinase genes on a replicative plasmid in *C. Albicans* and in *Saccharomyces cerevisiae*," 1992, *Mol. Gen. Genet.* 235:453-457.

Sierkstra et al., "Optimisation of a host/vector system for heterologous gene expression by *Hansenula polymorpha*," 1991, *Current Genetics*, 19:81-87.

Yang et al., "High Efficiency Transformation of *Pichia stipitis* Based on Its *URA3* Gene and a Homologous Autonomous Replication Sequence, *ARS2*," 1994, *Applied and Environ. Microbiology*, 60(12):4245-4254.

* cited by examiner pLNH31, pLNH32, pLNH33, or pLNH 34

Fermentation of Glucose and Xylose by LNH32

Simultaneous Fermentation of Glucose and Xylose by Recombinant Saccharomyces LNH33

Fermentation of Glucose and Xylose by the Un-Engineered Parent 1400 *Saccharomyces* Yeast Fermentation of glucose and xylose by LNH32 after being cultured for 4 and 20 generarions in non-selective (glucose) medium.

Fermentation of glucose and xylose by LNH33 after being cultured for 4 and 20 generations in non-selective (glucose) medium.

Fermentation of glucose and xylose by LNH-ST(1) after being cultured for 4, 20, and 40 generations in non-selective (glucose) medium.

(A) Yeast (S. cerevisiae) AH22 cultured in YEPD (1% yeast extracts, 2% peptone, 2% glucose or YEP (1% yeast extracts, 2% peptone).
(B) Yeast AH22 cultured in YEPXlu (1% yeast extracts, 2% peptone, 2% xylulose) or YEP.

Construction of pKS(−)−KK−AR−KD plasmids

†The XhoI site was regenerated after ligation; *Intact ADC1 promoter;
** ADC1 promoter with TRP5 ribosomal binding site Recombinant Saccharomyces 1400(LNH-ST) for fermenting Glucose and Xylose

STABLE RECOMBINANT YEASTS FOR FERMENTING XYLOSE TO ETHANOL

This application is a 371 of PCT/US97/07663, filed on May 6, 1997, and claims benefit to U.S. Provisional Application No. 60/016,865, filed May 6, 1996.

BACKGROUND

The present invention relates generally to genetically engineered microorganisms and in particular to unique methods for stably incorporating exogenous DNA into cells, including the incorporation of multiple copies of the exogenous DNA at reiterated DNA sequences in the host. In a preferred aspect, the invention relates to yeasts capable of fermenting xylose (preferably cofermenting the same with glucose) to ethanol. More particularly, a preferred aspect of the invention relates to yeasts containing cloned genes encoding xylose reductase (XR), xylitol dehydrogenase (XD), and xylulokinase (XK), which yeasts substantially retain their efficiency for fermenting xylose to ethanol even after culturing in non-selective medium for a large number of generations.

As further background, recent studies have proven ethanol to be an ideal liquid fuel for automobiles. It can be used directly as a neat fuel (100% ethanol) or as a blend with gasoline at various concentrations. The use of ethanol to supplement or replace gasoline can reduce the dependency of many nations on imported foreign oil and also provide a renewable fuel for transportation. Furthermore, ethanol has proven to provide cleaner fuels that release far fewer pollutants into the environment than regular gasoline. For example, it has been demonstrated that the use of oxygenated materials in gasoline can reduce the emission of carbon monoxide, a harmful pollutant, into the air. Among the several oxygenates currently used for boosting the oxygen content of gasoline, ethanol has the highest oxygen content. The United States Environmental Protection Agency (EPA) has shown that gasoline blended with 10% ethanol reduces carbon monoxide emissions by about 25%-30%.

Up to now, the feedstock used for the production of industrial alcohol by fermentation has been sugars from sugar cane or beets and starch from corn or other food crops. However, these agricultural crops are presently considered to be too expensive to be used as feedstock for the large-scale production of fuel ethanol. Plant biomass is an attractive feedstock for ethanol-fuel production by fermentation because it is renewable, and available at low costs and in large amounts. The concept of using alcohol produced by microbial fermentation of sugars from agricultural biomass had its nascence at least two decades ago. The major fermentable sugars from cellulosic materials are glucose and xylose, with the ratio of glucose to xylose being approximately 2 or 3 to 1. The most desirable fermentations of cellulosic materials would, of course, completely convert both glucose and xylose to ethanol. Unfortunately, even now there is not a single known natural microorganism capable of fermenting both glucose and xylose effectively.

Yeasts, particularly Saccharomyces yeasts, have traditionally been used for fermenting glucose-based feedstocks to ethanol, and they are still considered the best microorganisms for that purpose. However, these glucose-fermenting yeasts, including the Saccharomyces yeasts, have been found to be unable to ferment xylose and also unable to use this pentose sugar for growth.

Recently, N. Ho et al. have developed recombinant yeasts, particularly recombinant Saccharomyces yeasts, capable of effectively fermenting xylose to ethanol (Ho and Tsao, 1995). More particularly, the preferred recombinant yeasts were capable of co-fermenting the two major sugar constituents of cellulosic biomass, glucose and xylose, to ethanol (Ho and Tsao, 1995). These recombinant yeasts were developed by the transformation of yeasts with a high-copy number plasmid containing three cloned genes, XR, XD, and XK, encoding three key enzymes for xylose metabolism (FIG. 1). FIG. 2 and FIG. 3 demonstrate two of the prior-made recombinant Saccharomyces yeasts, designated 1400 (pLNH32) and 1400 (pLNH33), capable of co-fermenting 8% glucose and 4% xylose present in the same medium almost completely to ethanol in two days. On the other hand, FIG. 4 shows that the parent yeast fusion 1400 (D'Amore, et al., 1989 and D'Amore, et al., 1990) can only ferment glucose, but not xylose, to ethanol. 1400 (pLNH32) (in short LNH32) and 1400 (pLNH33) (in short LNH33) were developed by the transformation of the Saccharomyces fusion 1400 (D'Amore, et al., 1989 and D'Amore, et al., 1990) with two of the high-copy-number plasmids, pLNH32 and pLNH33, shown in FIG. 1. To date, there have been four such high-copy-number plasmids reported, pLNH31, pLNH32, pLNH33, and pLNH34 (Ho and Tsao, 1995). Each of these plasmids can transform fusion 1400 to recombinant yeasts to co-ferment both glucose and xylose with similar efficiencies.

Yeasts 1400 (pLNH32), 1400 (pLNH33), and related recombinant xylose-fermenting Saccharomyces, with their xylose metabolizing genes cloned on a 2µ-based stable high-copy-number plasmid, are quite suitable for a batch process fermentation. However, in a continuous process fermentation, after prolonged culture in a glucose-rich medium (more than 20 generations), 1400 (pLNH32), 1400 (pLNH33), and similar plasmid-mediated recombinant yeasts lose their capability of fermenting xylose as shown in FIG. 5 and FIG. 6.

Generally, exogenous DNA or gene(s) can be cloned into yeasts by two separate ways. One way is to clone the exogenous DNA or gene(s) into a plasmid vector containing a selectable genetic marker and a functional yeast DNA replication origin or ARS (autonomous replicating sequence) (Struhl et al., 1979; Stinchcomb et al., 1980; Chan and Tye, 1980) that allows the plasmid to be able to replicate autonomously in its new host, followed by transformation of the desired yeast host with the plasmid containing the cloned DNA fragment or gene(s). The resulting yeast transformants are able to stably maintain the cloned gene in the presence of selection pressure. However, such cloned gene(s) are unstable after prolonged culture in non-selective medium (in the absence of selection pressure).

Another way to clone the exogenous DNA or gene(s) into a yeast host is to integrate the DNA or gene(s) into the yeast chromosome. In yeast, integrative transformation is almost always via homologous recombination (Orr-Weaver, 1981). The simplest way to clone a desired gene into a yeast chromosome by integration is first to clone the desired gene into a plasmid which does not contain a replication of origin or ARS (autonomous replication sequences) but does contain a piece of the host DNA for targeting the integration to a specific site (Orr-Weaver, 1981). Transformation of the new yeast host with such an intact integrative vector will generate integrative transformants containing the desired gene cloned to the site next to the selected targeting yeast DNA sequences. However, the frequency of such integrative transformation is extremely low (1 to 10 transformants per µg DNA). Subsequently, it has been demonstrated that integrative vectors linearized within the DNA fragment homologous to the host chromosomal DNA can transform yeasts with much higher frequencies (100-to 1000-fold higher) (Orr-Weaver, 1981; Orr-Weaver and Szostak, 1983). It was suggested that double-stranded breaks, introduced by restriction enzyme digestion, are recombinogenic and highly interactive with homologous chromosomal DNA. This is particularly helpful for a complex plasmid, containing more than one yeast gene, so that one can direct the integration to a specific site by making a restriction enzyme cut within the corresponding region on the plasmid.

Another type of integration, also described as transplacment or gene disruption, makes use of double homologous recombination to replace yeast chromosomal DNA (Rothstein, 1981). Double homologous recombination vectors contain the exogenous DNA or gene(s) to be cloned and the selection marker, flanked by yeast DNA sequences homologous to 5' and 3' regions of the segment of chromosomal DNA to be replaced. Prior to transformation, the vector is digested with restriction enzymes which liberate the transplacing fragment containing 5' and 3' ends homologous to the chromosomal DNA sequences at the desired integration sites. The latter strategy has become the method of choice for integrative transformation of yeast if a stable single-copy transformant is desired.

A number of strategies based on integration into reiterated chromosomal DNA have been used to generate stable multiple-copy integrants. For example, the delta sequence of yeast retrotransposon Ty (Sakai et al., 1990; Sakai et al., 1991), the highly conserved repeated sigma element (Kudla and Nicolas, 1992) and non-transcribed sequences of ribosomal DNA (Lopes et al., 1989; Lopes et al., 1991; Rossolini et al., 1992) have all been used as the target sites for multiple integration of exogenous gene(s) into yeast (Rothstein, 1991; Romanos et al., 1992).

Recent work reported in the literature on multiple integration of exogenous genes into the yeast chromosome has for the most part involved the use of either properly linearized non-replicative vectors or DNA fragments containing the desired gene(s) to be cloned and the genetic marker for selection, flanked with DNA sequences homologous to a region of yeast chromosomal DNA. Rarely, linearized replicative vectors and almost never intact replicative vectors, such as intact ARS vectors, were used to achieve such recombinant transformation. Thus, since early work at the onset of developing yeast integrative transformation, (Szoatak and Wu (1979)), and despite the observation that DNA cloned on ARS vectors can integrate into the host chromosomes (Cregg et al., 1985; Kurtz et al., 1986), the use of intact ARS vectors (Struhl et al., 1979; Stinchcomb et al., 1980; Chan and Tye, 1980) for integration purposes has long since generally been abandoned. This has especially been true since the discovery that the double-stranded breaks introduced by restriction enzyme digestion are recombinogenic (Orr-Weaver, 1981; Orr-Weaver and Szostak, 1983).

In light of this background, there remain needs for more stable yeast which ferment xylose to ethanol, preferably xylose and glucose simultaneously to ethanol, and for facile and effective methods for making high copy number integrants. The present invention addresses these needs.

SUMMARY OF THE INVENTION

Accordingly, the present invention provides yeast containing multiple copies of stably cloned XR, XD, and XK genes, which even upon culture in non-selective medium for multiple generations (e.g. greater than 20) retain their full capability to ferment xylose to ethanol. More preferably, the XR, XD, and XK genes are all fused to promoters not inhibited by the presence of glucose and also not requiring the presence of xylose for their expression. Still more preferably, the yeast of the invention can co-ferment the two major constituents of cellulosic biomass, glucose and xylose, to ethanol.

Another embodiment of the present invention relates to the use of reiterated sequences, e.g. non-transcribed r-DNA sequences adjacent to the 5S DNA (Valenzuela et al., 1977), as homologous sequences for targeting high-copy-number integration of a DNA fragment containing XR, XD, and XK into the yeast genome via homologous recombination. For example, a replicative plasmid vector including the DNA fragment flanked by the homologous sequences can be used to target integration of the DNA fragment. A preferred method of the invention includes the steps of (a) transforming the cells with a replicative/integrative plasmid having exogenous DNA including a selection marker; and (b) repeatedly replicating the cells from step (a) to produce a number of generations of progeny cells while selecting for cells which include the selection marker (e.g. by replicating on selective plates), so as to promote the retention of the replicative and integrative plasmid in subsequent generations of the progeny cells and the formation of progeny cells having multiple integrated copies of the exogenous DNA. In a further step, the cells from step (b) can be replicated to produce a number of generations of progeny cells in the absence of selection for cells which include the selection marker, so as to promote the loss of the plasmid in subsequent generations of progeny cells (thus leaving an enriched population of the stable integrants).

The invention also provides an advantageous mode for selection and maintenance of the desired transformants. It is well known that in minimal medium all microorganisms require the presence of a carbon source, such as glucose or xylose, for growth. However, most microorganisms do not require the presence of a carbon source for growth in rich medium. Nevertheless, the present invention provides the use a carbon source as the selection pressure for the selection of transformants even in rich medium, such as YEP (1% yeast extract plus 2% peptone). The development of stable transformants, such as 1400 (LNH-ST) (FIG. 7), which are capable of effective fermentation of xylose after culturing in non-selective medium for essentially unlimited generations, has been greatly facilitated by the discovery that many yeasts, particularly *Saccharomyces* yeasts, do naturally require the presence of a carbon source, such as xylose or glucose, for growth even in rich medium, as shown in FIG. 8.

In a broad aspect, the invention also provides a method for integrating multiple copies of exogenous DNA into reiterated chromosomal DNA of cells. The method includes (a) transforming the cells with a replicative and integrative plasmid having exogenous DNA including a selection marker. The method also includes (b) replicating the cells from step (a) to produce a number of generations of progeny cells while selecting for cells which include the selection marker, so as to promote the retention of the replicative and integrative plasmid in subsequent generations of the progeny cells and produce progeny cells having multiple integrated copies of the exogenous DNA. In a specific application, such a method includes (i) transforming yeast cells with a replicative plasmid having exogenous DNA including a selection marker, the exogenous DNA being flanked on each end by a DNA sequence homologous to a reiterated sequence of DNA of the host; (ii) repeatedly replicating the transformed yeast cells from step (i) to produce a number of generations of progeny cells while selecting for cells which include the selection marker, so as to promote the retention of the replicative plasmid in subsequent generations of the progeny cells and result in progeny cells each containing multiple integrated copies of the exogenous DNA; and (iii) replicating the progeny cells from step (ii) to produce a number of generations of progeny cells in the absence of selection for cells which include the selection marker, so as to promote the loss of the plasmid in subsequent generations of progeny cells and recover yeast cells each containing multiple copies of the exogenous DNA integrated into its chromosomal DNA.

In still another embodiment, the invention provides a yeast which ferments xylose to ethanol, the yeast having multiple copies of exogenous DNA integrated into its chromosomal DNA. The exogenous DNA including genes encoding xylose reductase, xylitol dehydrogenase, and xylulokinase fused to non-glucose-inhibited promoters, wherein the yeast ferments glucose and xylose simultaneously to ethanol and substantially retains its capacity for fermenting xylose to ethanol for at least 20 generations even when cultured under non-selective conditions.

Another aspect of the invention relates to methods for fermenting xylose to ethanol, which include fermenting xylose-containing mediums with yeasts of the invention.

Another embodiment of the invention provides a plasmid vector for integrating an exogenous DNA sequence including a selection marker into chromosomal DNA of a target yeast cell. The inventive plasmid vector contains a functional yeast DNA replication origin and the exogenous DNA including the selection marker flanked on each end by a DNA flanking sequence which is homologous to a reiterated ribosomal DNA sequence of the target yeast cell. The plasmid further has a second selection marker in a position other than between the DNA flanking sequences.

A still further embodiment of the invention provides a plasmid vector for integrating an exogenous DNA sequence into a yeast to form stable integrants which ferment xylose to ethanol. The vector contains a functional yeast DNA replication origin and exogenous DNA including genes encoding xylose reductase, xylitol dehydrogenase, and xylulokinase flanked on each end by a DNA flanking sequence which is homologous to a reiterated DNA sequence of the target yeast cell.

A still further aspect of the invention provides a method for forming cells having multiple integrated copies of an exogenous DNA fragment. This inventive method includes replicating cells having reiterated genomic DNA and which contain a replicative and integrative plasmid containing the exogenous DNA to produce multiple generations of progeny cells while selecting for cells which include the selection marker, so as to promote the retention of the replicative and integrative plasmid in subsequent generations of the progeny cells and produce progeny cells having multiple integrated copies of the exogenous DNA.

The invention provides yeasts containing stably cloned genes enabling their use under non-selective conditions (e.g. continuous fermentations) to coferment xylose and glucose to ethanol, while not losing their capacity to ferment xylose. In addition, the invention provides methods and materials for forming stable, multiple-copy integrants of yeast and other cells which are facile to perform and which can be controlled to modulate the number of copies of the integrated exogenous DNA. Additional embodiments, and features and advantages of the invention will be apparent from the following description and appended claims.

DETAILED DESCRIPTION OF THE INVENTION

For the purpose of promoting an understanding of the principles of the invention, reference will now be made to certain preferred embodiments thereof, and specific language will be used to describe the same. It will nevertheless be understood that no limitation of the scope of the invention is thereby intended, such alterations, further modifications and applications of the principles of the invention as described herein are being contemplated as would normally occur to one skilled in the art to which the invention relates.

As mentioned above, one preferred aspect of the present invention provides recombinant yeasts incorporating stably cloned XR, XD and XK genes, which represent an improvement upon prior-reported recombinant yeasts. Generally, recombinant yeasts that can effectively coferment both glucose and xylose present in the same medium have been reported (Ho and Tsao, 1995).

Figure 1:
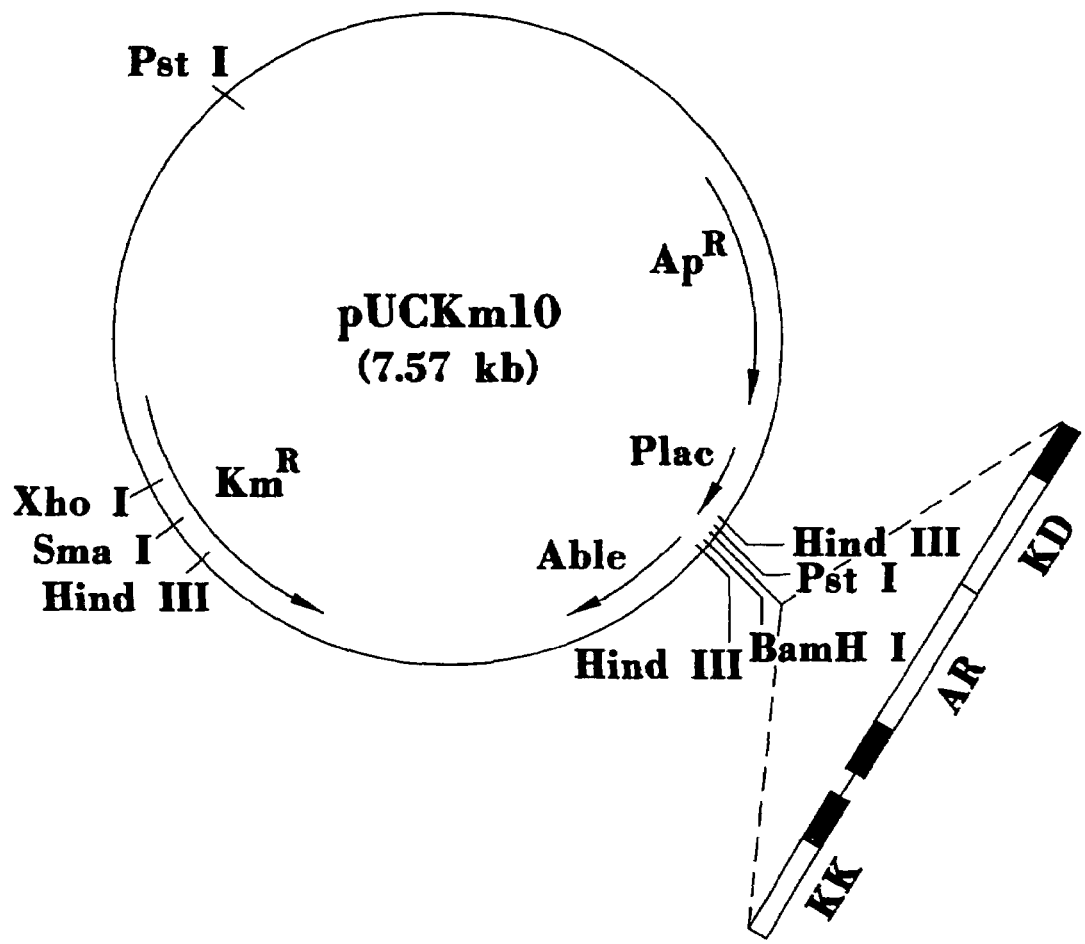
FIG. 1 shows the restriction map of the plasmids pLNH31, -32, -33, and -34, and the genes cloned within.
Figure 2:
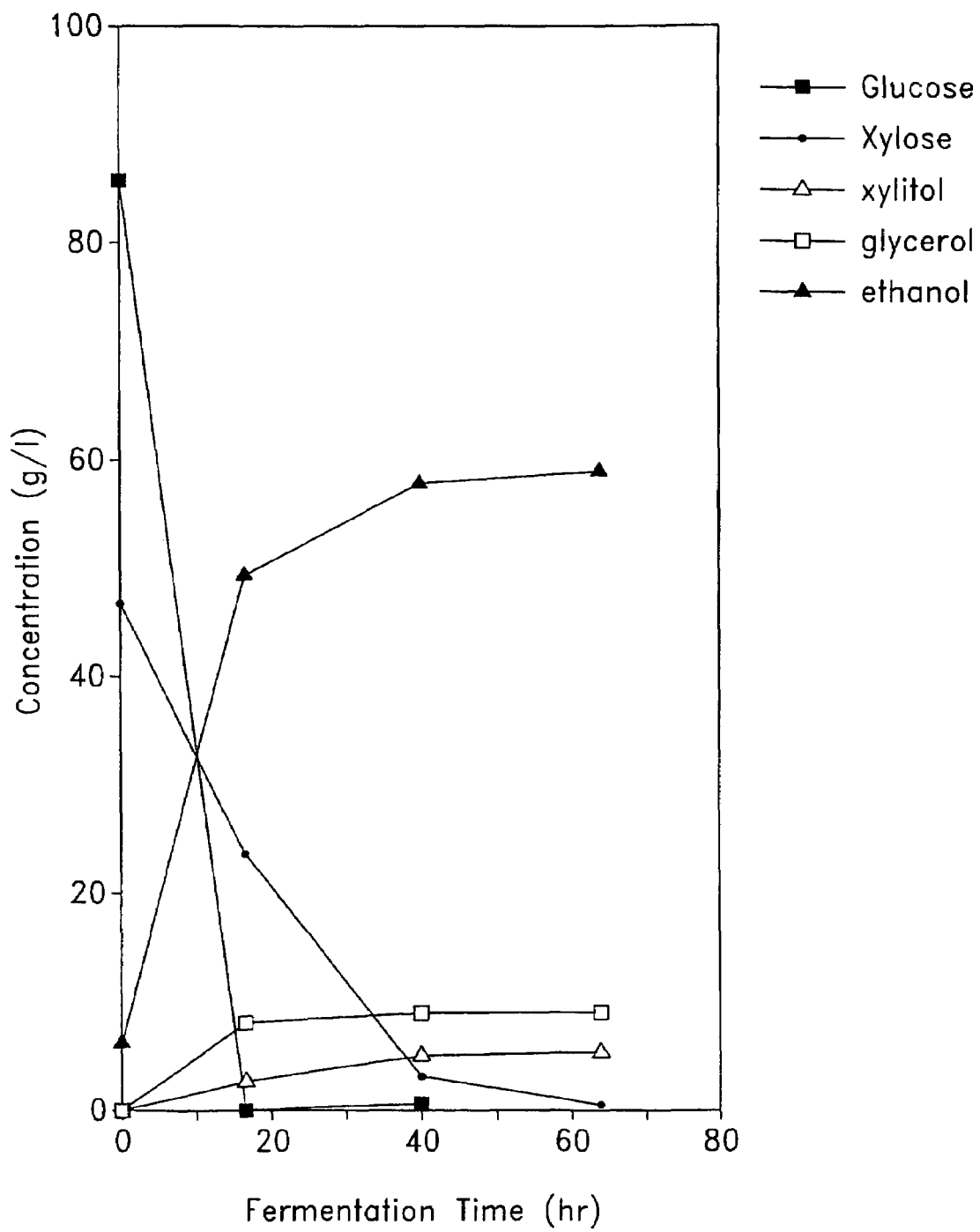
FIG. 2 shows that yeast transformant 1400 (pLNH32) (in short LNH32) can effectively coferment glucose and xylose. The conditions used for culturing the yeast and for fermenting the sugars are similar to those described in Example 7.
Figure 3:
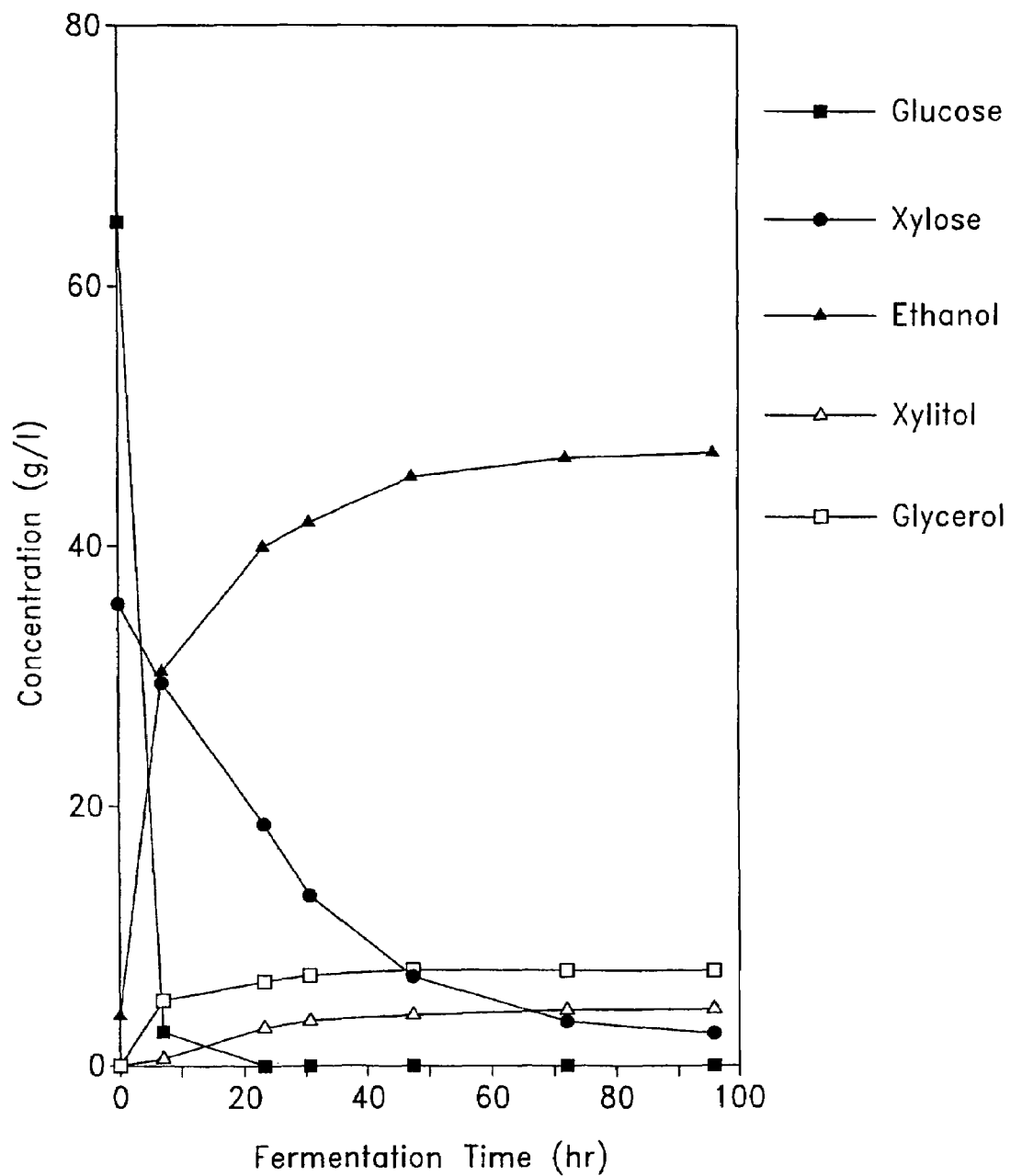
FIG. 3 shows that yeast transformant 1400 (pLNH33) (in short LNH33) can effectively coferment glucose and xylose. The conditions used for culturing the yeast and for fermenting the sugars are similar to those described in Example 7.
Figure 4:
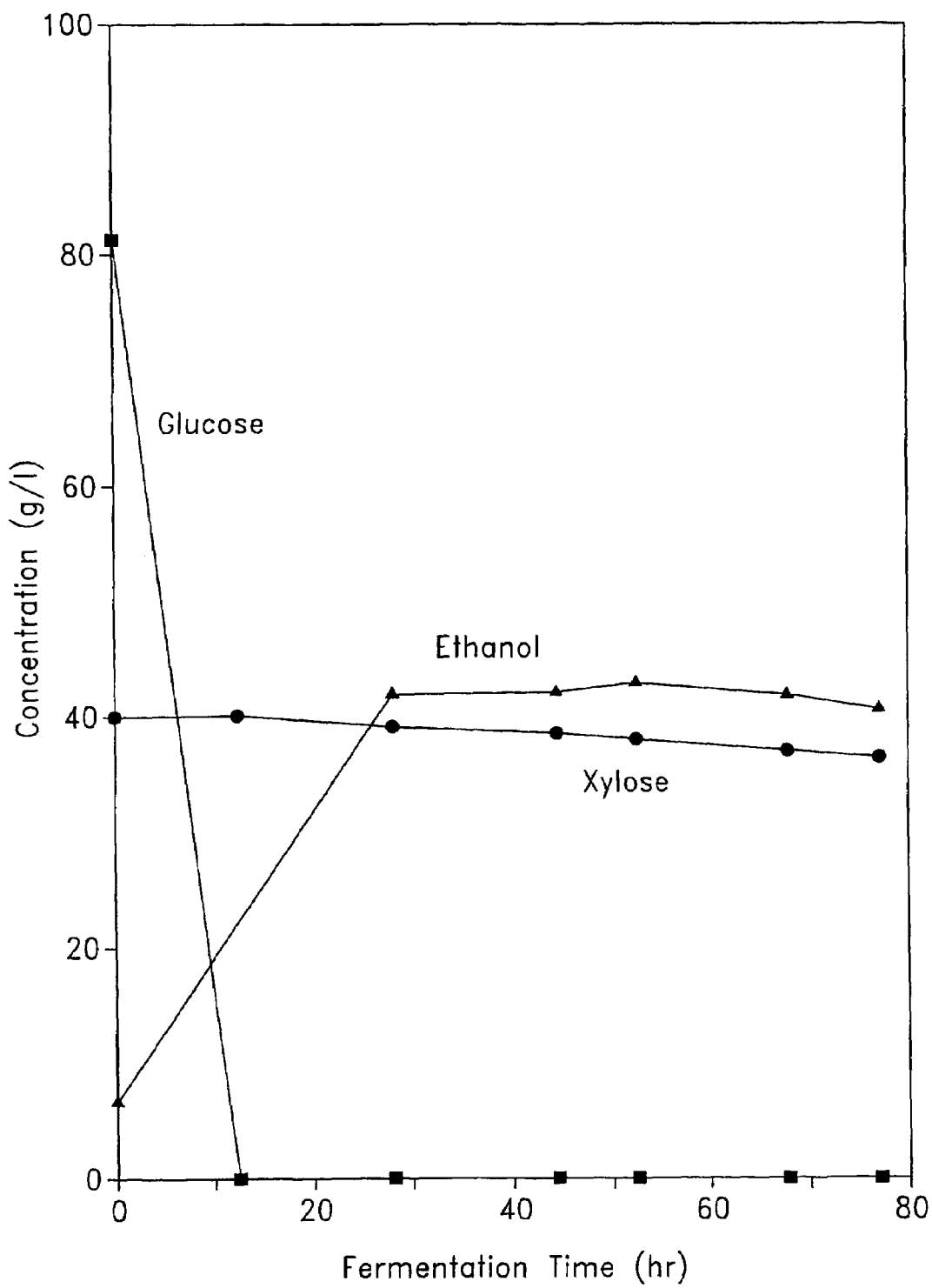
FIG. 4 shows that the parent yeast fusion strain 1400 can ferment glucose but not xylose. The conditions used for culturing the yeast and for fermenting the sugars are similar to those described in Example 7.

The yeasts made in this publication were accomplished by cloning properly modified XR, XD, and XK genes on a high copy number plasmid, pUCKm10, followed by using the resulting plasmid, pLNH3X (X=1 to 4) (FIG. 1), to transform suitable natural yeasts. For example, the plasmids pLNH32 and pLNH33 were used to transform fusion yeast 1400 to 1400 (pLNH32) and 1400 (pLNH33), respectively. These recombinant *Saccharomyces* yeasts can effectively coferment both glucose and xylose present in the same medium to ethanol as shown in FIGS. 2 and 3, while the parent unengineered 1400 yeast can only ferment glucose alone, not coferment both glucose and xylose (FIG. 4).

Plasmid-mediated recombinant yeasts can maintain the cloned genes in the presence of selection pressure, but not in the absence of selection pressure. As demonstrated in FIGS. 5 and 6, 1400 (pLNH32) and 1400 (pLNH33) eventually lose their plasmids and their capability for fermenting xylose after prolonged culture in the absence of selection pressure.

It is highly desirable that recombinant industrial yeasts, particularly those strains used for the production of large volume industrial products, such as ethanol, be stable without requiring the presence of selection. The development of recombinant yeasts containing integrated XR, XD, and XK genes, as in the present invention, provides such stability. In addition, for the resulting recombinant yeasts to have the ability to coferment glucose and xylose at efficiencies similar to or better than 1400 (pLNH32) and 1400 (pLNH33), the recombinant yeasts must contain not only the integrated xylose metabolism genes, but also high numbers of copies of such integrated genes. In preferred aspects of the present invention, high-copy-number (hcn) integrants of yeasts (i.e. yeasts having at least about 10 integrated copies of the exogenous DNA) have been developed by targeting a non-coding region, such as a non-coding region of 5S ribosomal DNA (rDNA) as the site for multiple integration.

rDNA provides an advantageous location for integration because it is highly conserved, and yeasts generally contain more than 100 copies of the rDNA repeated sequences. It will be understood, however, that to achieve yeasts of the present invention, it will not be necessary to achieve integration of the desired genes at every occurrence of a repeated or reiterated sequence. It will be sufficient to achieve such integration at each of multiple sites of a reiterated sequence, i.e. two or more sites, in accordance with the broad aspects of the present invention.

Figure 9A:
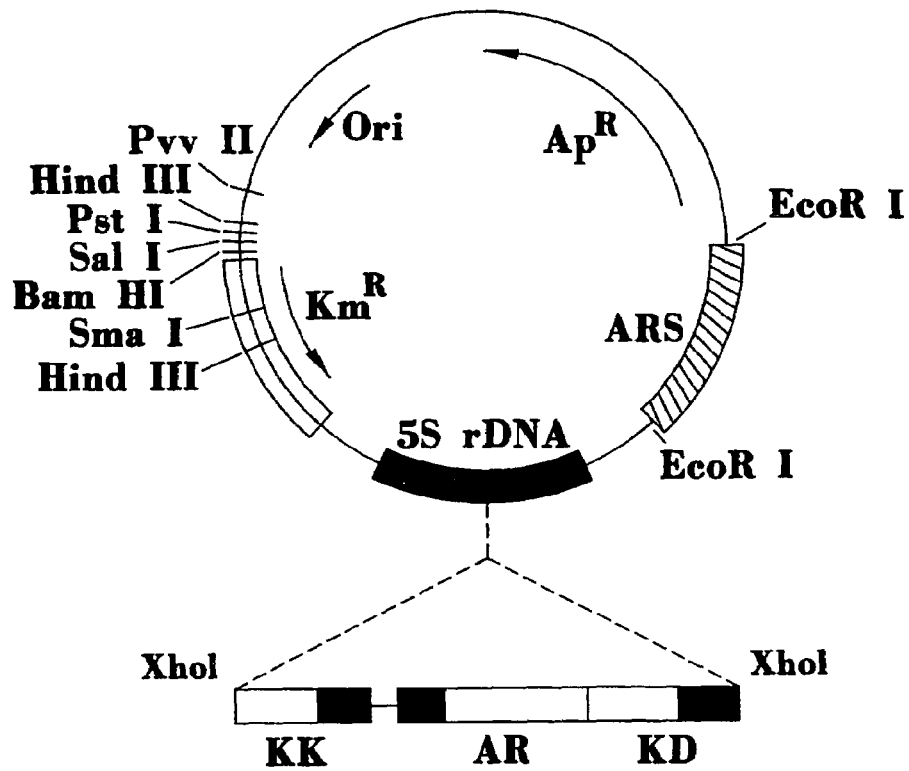
FIG. 9A shows the restriction map of pLNH-ST, and the genes cloned within.

In order to integrate hcn XR, XD, and XK into the yeast chromosome at the site of 5S rDNA, the integration plasmid, pLNH-ST, as shown in FIG. 9, was constructed. pLNH-ST is a yeast-*E. coli* shuttle vector and a derivative of pUCKm 6 plasmid (Ho et al., 1984). The 5S rDNA sequences was inserted at the XhoI restriction site of pUCKm 6. The 5S rDNA sequence was copied from the yeast chromosomal DNA by the PCR technique and modified by the site-specific mutagenesis technique to add an XhoI restriction site in its center (approximately) sequence as shown in FIG. 9. The XhoI fragment from pKS(−)-KK-AR-KD (FIG. 10) (Ho and Tsao, 1995) has been inserted into the XhoI site of the 5S rDNA cloned in PLNH-ST.

pLNH-ST differs from other traditional 5S rDNA-based hcn yeast integrating vectors in that it also contains a functional yeast ARS sequence (Struhl et al., 1979; Stinchcomb et al., 1980; Chan and Tye, 1980) as shown in FIG. 9. Thus, pLNH-ST is both a replicative vector and an integrative vector. Uniquely, pLNH-ST functions first as a replicative vector then as an integrative vector in the development of recombinant yeasts containing high copies of integrated XR, XD, and XK. The ARS fragment was inserted at the EcoR1 site of pUCKm 6. In addition, pLNH-ST also contains the kanamycin resistance gene ($Km^R$) and the ampicillin resistance gene ($Ap^R$). $Km^R$ functions as a geneticin resistance gene in yeasts and will confer its yeast transformants resistant to geneticin. The XhoI site of $Km^R$ was removed by PCR technique without affecting its activity. Both $Km^R$ and $Ap^R$ are part of the original pUCKm 6 plasmid.

As noted above, the above-described vectors differ from those used in state-of-the-art techniques by containing an ARS sequence. In addition, in prior-reported methods for making hcn yeast integrants, integration of the cloned genes has taken place instantly, at the moment when the yeast cells are transformed with the exogenous genes. To the contrary, in accordance with preferred modes of the invention, integration of the cloned genes continues to take place gradually, long after transformation has been completed. In particular, transformation is established first via the presence of replicative plasmid, such as pLNH-ST, in the transformed yeast cells, and integration takes place only gradually via repeated replication of the transformants on plates containing selective medium.

Figure 5:
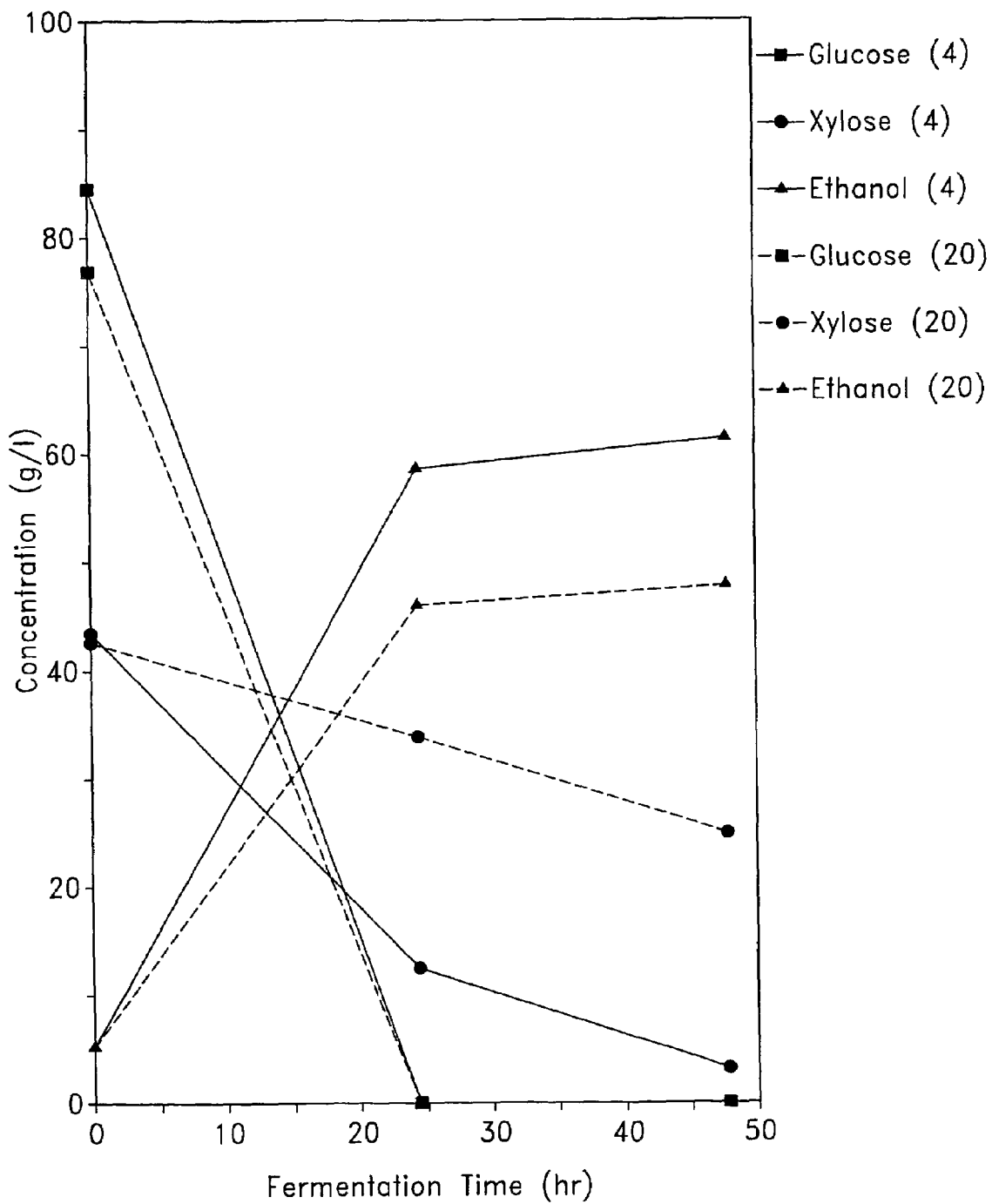
FIG. 5 demonstrates that yeast transformant 1400 (pLNH32) (in short LNH32) with its xylose metabolizing genes cloned in the replicative plasmid pLNH 32 is not stable in a non-selective medium. After being cultured for 20 generations in a non-selective (for example, glucose) medium, 1400 (pLNH32) lost its capability to ferment xylose.
Figure 6:
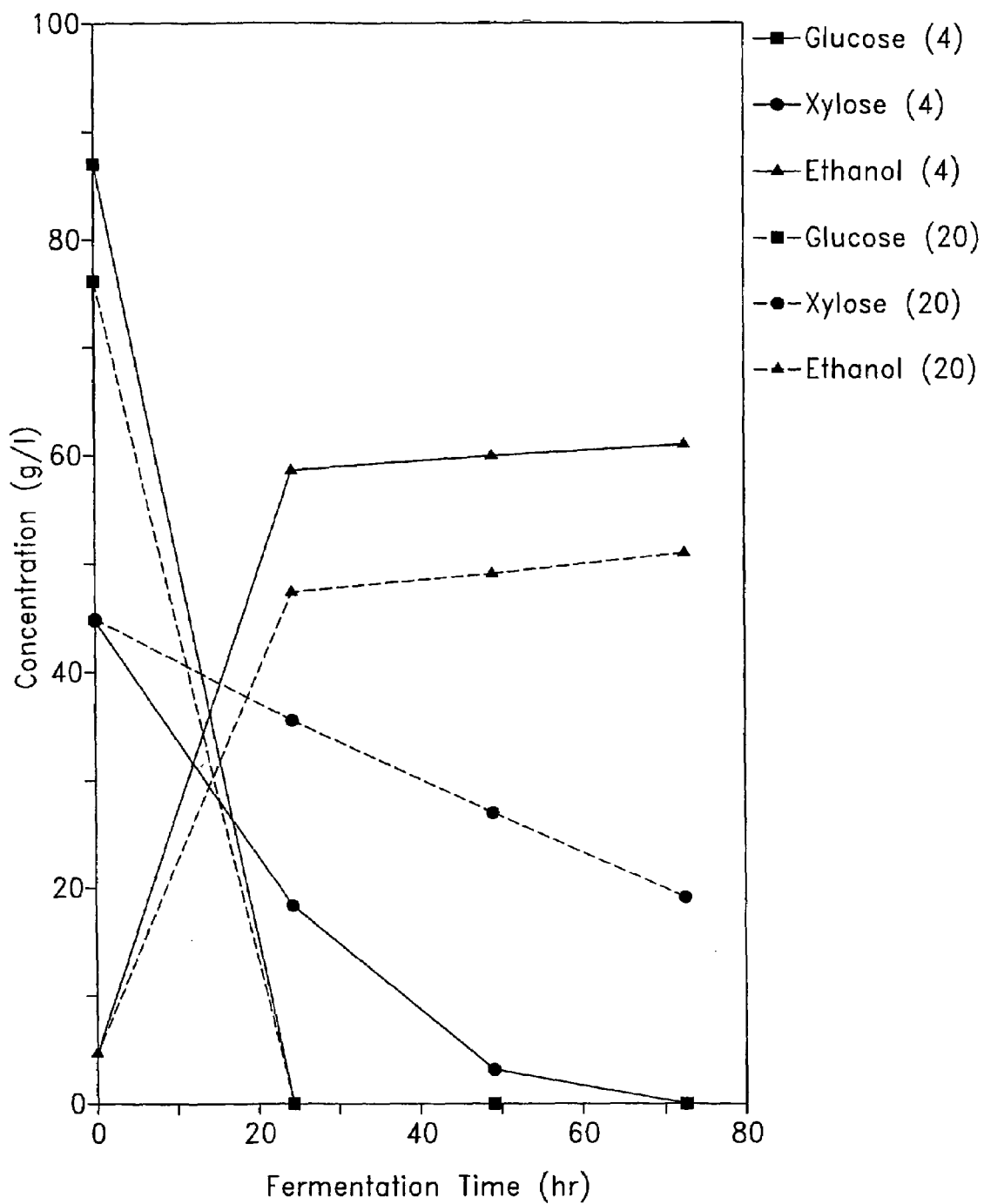
FIG. 6 demonstrates that yeast transformant 1400 (pLNH33) (in short LNH33) with its xylose metabolizing genes cloned in the replicative plasmid pLNH 33 is not stable in a non-selective medium. After being cultured for 20 generations in a non-selective medium (for example, glucose medium), 1400 (pLNH33) lost its capability to ferment xylose.
Figure 7:
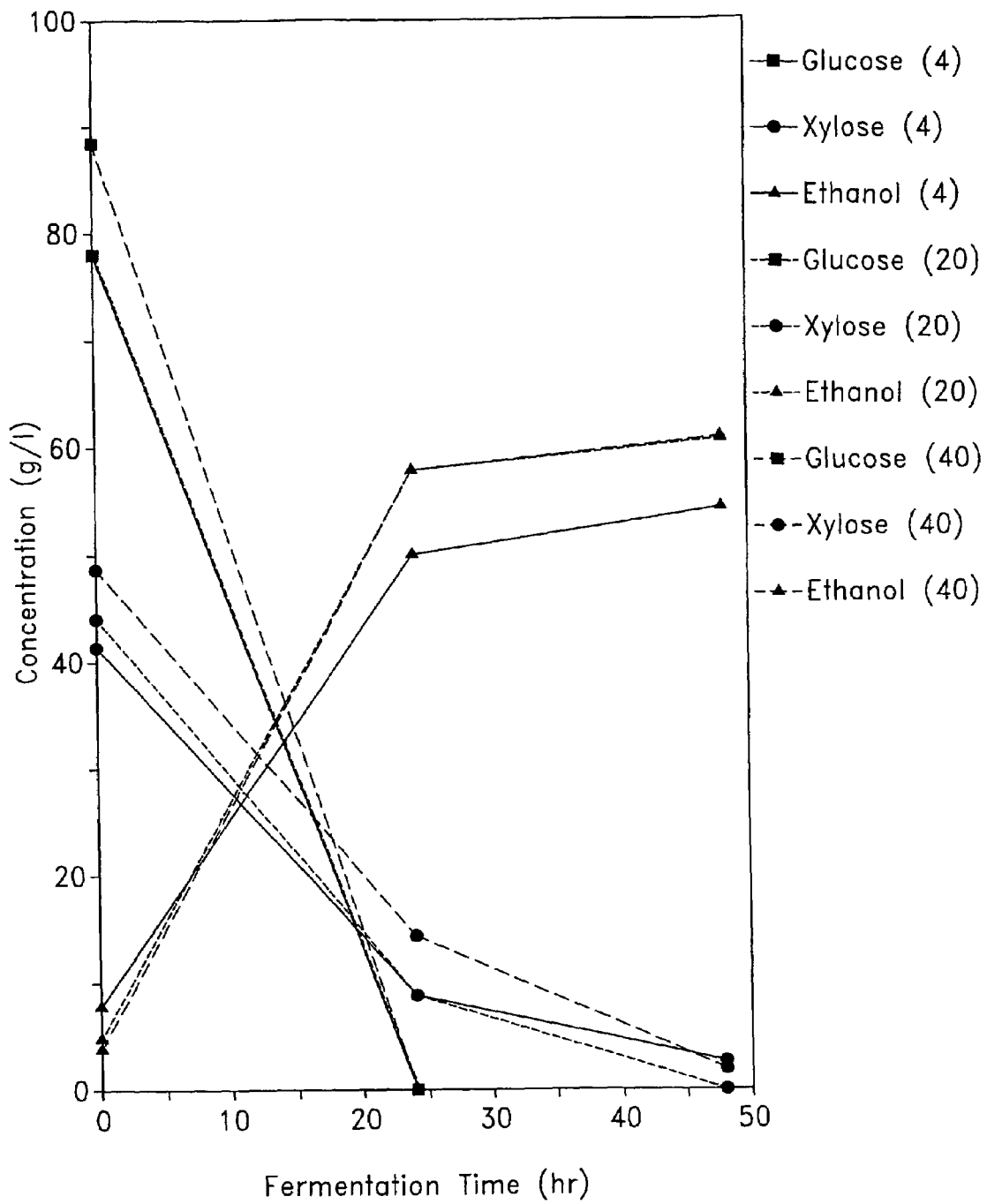
FIG. 7 shows that yeast transformant 1400 (LNH-ST) (in short LNH-ST) can stably maintain its xylose fermenting capability even after being cultured in non-selective medium for more than 40 generations.
Figure 11:
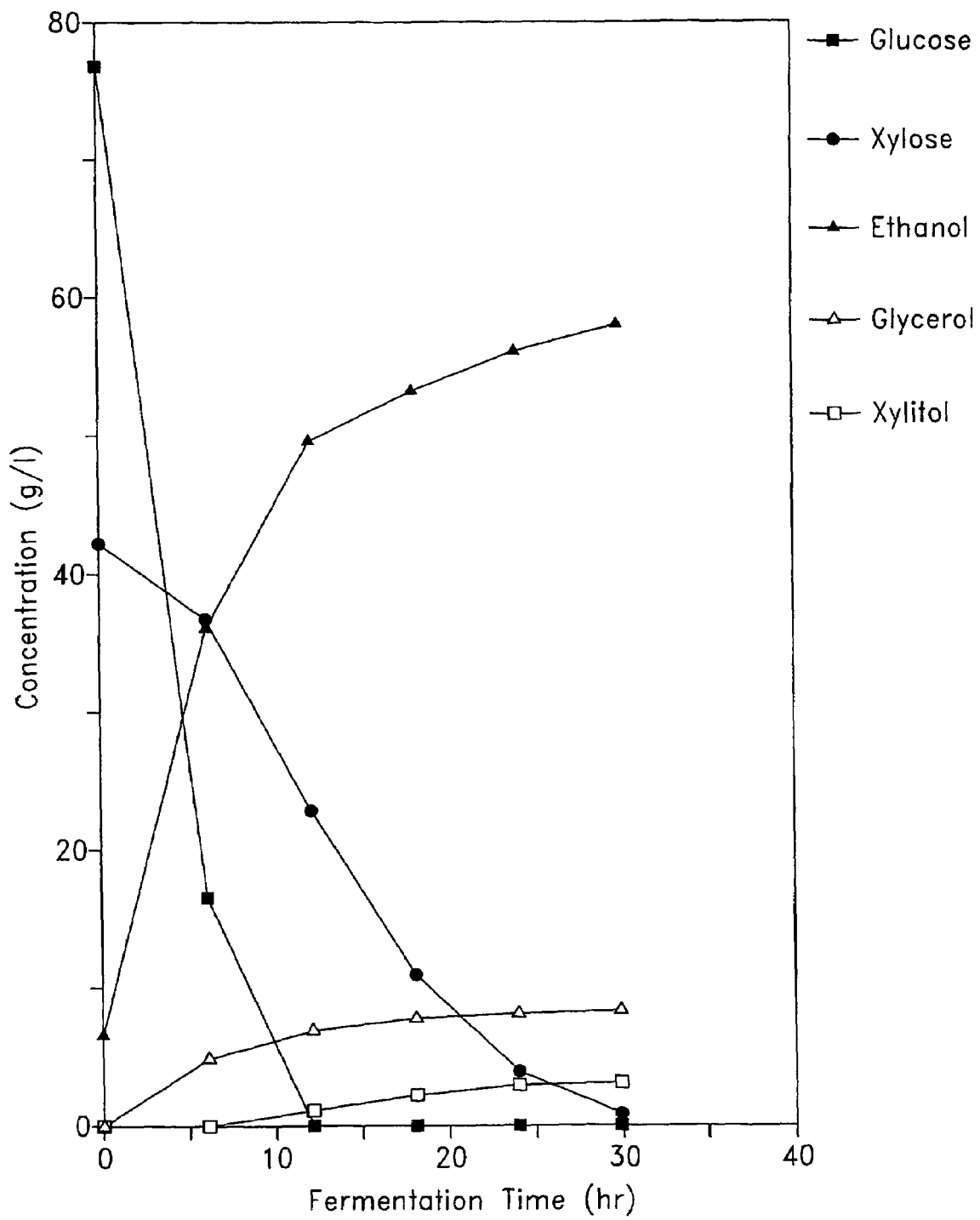
FIG. 11 shows that yeast transformant 1400 (LNH-ST) (in short LNH-ST), superior to 1400 (pLNH 32) and 1400 (pLNH 33), can effectively coferment glucose and xylose. The conditions used for culturing the yeast and for fermenting the sugars are similar to those described in Example 7.

Thus, this invention relates the use of the following procedures to develop yeast or other cell transformants containing hcn integrated cloned gene(s). Host cells which contain reiterated DNA sequences, for example yeast or eukaryotic cells, are transformed with a replicative/integrative plasmid, such as pLNH-ST, and transformants containing high-copy numbers of the replicative/integrative plasmid are selected. The resulting selected transformants are repeatedly replicated onto fresh selective plates and grown to high cell density for a sufficient number of times to integrate the desired number of copies of the exogenous DNA, followed by culturing the transformants in non-selective medium for a sufficient number of generations to remove the replicative/integrative plasmids from the transformants. The resulting transformants can then be cultured in selective medium, and those transformants retaining their capability to effectively grow in selective medium will be those that contain hcn of the desired exogenous genes integrated into the chromosome of the yeast or other host cells. For example, fusion 1400 yeast has been transformed with pLNH-ST according to the above described procedures, and the resulting stable recombinant yeast, 1400 (LNH-ST), can coferment both glucose and xylose better than 1400 (pLNH 32) and 1400 (pLNH33), as shown in FIG. 11. Importantly, the newly-developed stable recombinant yeast, 1400 (LNH-ST), can still ferment both glucose and xylose with equal efficiencies after being cultured in non-selective medium for 4, 20, and 40 generations as shown in FIG. 7, while 1400 (pLNH 32) and 1400 (pLNH33) will lose most of their activity for fermenting xylose after 20 generations of being cultured in non-selective medium (FIGS. 5 and 6). Furthermore, 1400 (LNH-ST) has subsequently been cultured in non-selective medium for several hundred generations, and still retains its full activity in cofermenting both glucose and xylose.

Figure 8:
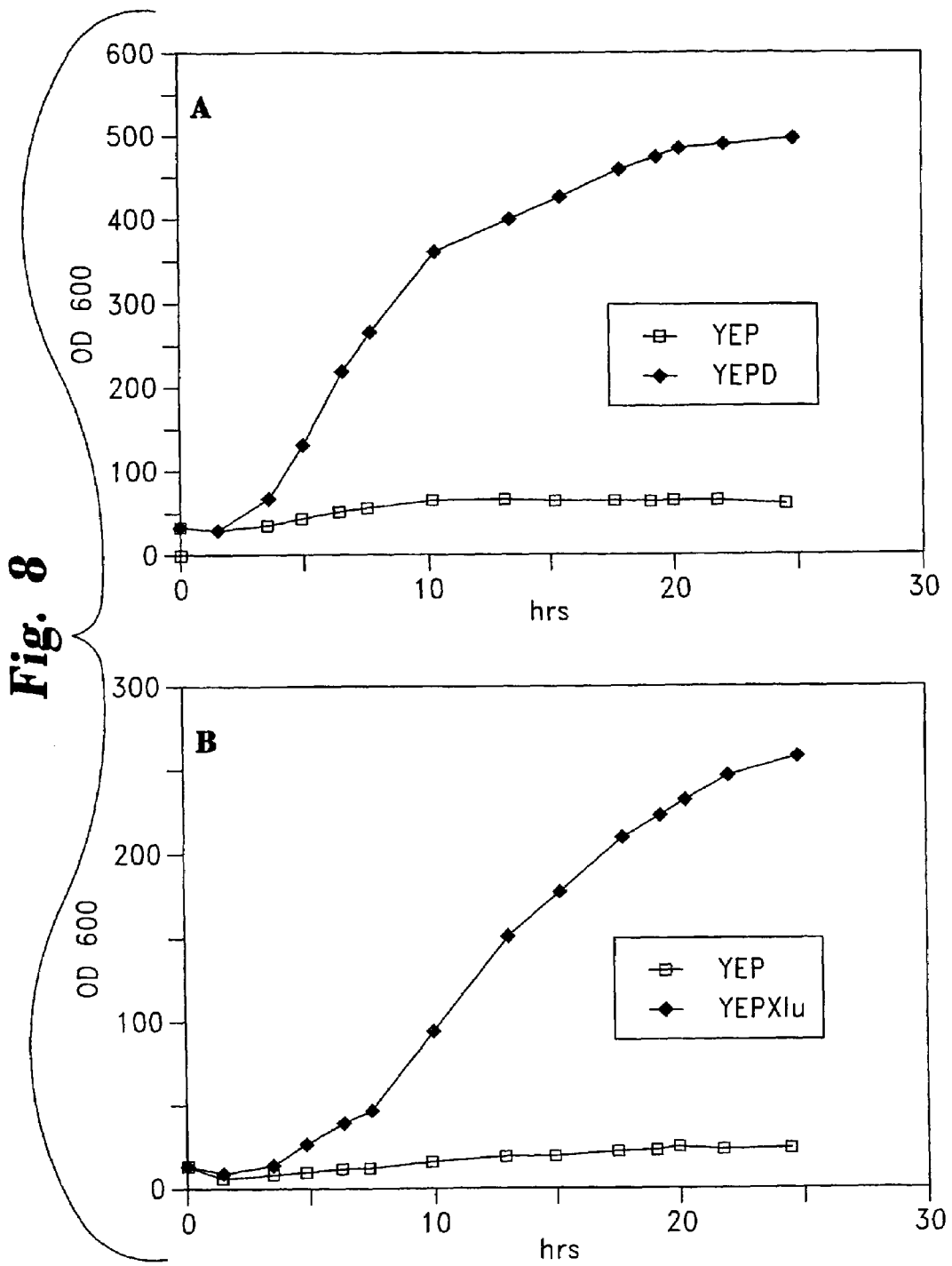
FIG. 8 demonstrates that *S. cerevisiae* and other *Saccharomyces* yeasts require a carbon source for growth even when rich media such as yeast extract and pepton were present in the medium. For example, these experiments showed that *S. cerevisiae* was unable to grow in the YEP medium containing 1% yeast extract and 2% pepton, but was able to grow when glucose or xylulose was added to the YEP medium.

In the preferred methods for developing stable hcn integrants, a common selection marker(s) is/are used for the selection and maintenance of both the plasmid-mediated activity and the activity contributed by the integrated genes with the same selective medium. In the present work, the common selection markers are the three cloned xylose metabolism genes, XR, XD, and XK, and the common selective medium is either rich or minimal medium (for yeasts) containing xylose. In addition, these cloned genes serve as the selection markers in rich medium for most *Saccharomyces* yeasts, since the applicants have shown that most of the *Saccharomyces* yeasts do require the presence of a carbon source, such as xylose, for growth even in rich medium (FIG. 8). Although it is not crucial for yeasts chosen as hosts to require the presence of a carbon source in rich medium for growth, it is, nevertheless, much more convenient to be able to select the desired integrants on plates containing rich medium with xylose rather than on plates containing minimal medium with xylose. Preferred hosts for transformation in the present invention belong to the *Saccharomyces* species, since they are usually extraordinarily effective for fermenting glucose. In the event that species of yeasts desired for use as hosts for integrating high copy numbers of xylose metabolizing genes are found not to require the presence of a carbon source for growth in rich medium, a suitable mutant of that species which does require the carbon source in rich medium can be isolated using conventional procedures.

The replicative/integrative plasmid, such as PLNH-ST, for achieving hcn integration also desirably contains a second selection means for the selection of replicative plasmid-mediated transformants. For pLNH-ST, the second selection mechanism utilizes both $Km^R$ and $Ap^R$ as selectable markers. Although it is not crucial for a replicative/integrative vector to contain a second selection system, it will provide more preferred vectors, particularly if the ARS vector is not sufficiently stable even in the presence of the selection pressure, and the transformants have the tendency to lose most of their plasmids prior to integrating sufficient copies of the desired genes. When using vectors which contain a second selection mechanism, the transformants may be cultured in the presence of the second selective reagent to boost their plasmids' copy number, or to re-transform the transformants with the same vector but using the second selection mechanism to re-select the transformants so that the integration process can be continued or re-initiated.

The use of both $Km^R$ and $Ap^R$ as the second selection system is desirable for the applicants' preferred yeast. $Km^R$ can be a dominant selection marker for transforming yeasts that are resistant to geneticin, but some yeasts are naturally resistant to geneticin without acquiring the plasmid containing $Km^R$. As a result, $Km^R$ alone is not a preferred selection marker for the selection of yeast transformants. On the other hand, $Ap^R$ can be effectively expressed in most yeasts, but it generally cannot be used as a dominant selection marker for yeast transformation because most yeasts are naturally resistant to ampicillin. However, both $Km^R$ and $Ap^R$ together serve as an excellent dominant selection system for most yeasts, particularly the *Saccharomyces* yeasts. To use such a selection system, the transformants are first selected on plates containing YEPD (1% yeast extract, 2% peptone, 2% glucose) and proper concentrations of geneticin (20-80 µg/ml, varying from species to species). The resulting transformants are screened for the expression of the $Ap^R$ by the penicillinase test (Chevallier and Aigle, 1979) to identify true transformants.

The presence of $Ap^R$ in pLNH-ST (FIG. 9) and related replicative/integrative plasmids also serves another function. Since $Ap^R$ is only present in the replicative plasmid and not present on the fragment integrated into the yeast chromosome, the ampicillin test also serves as a convenient process for identifying those transformants containing hcn integrated cloned genes but not plasmid vectors.

A feature of the inventive approach for providing stable recombinant yeasts containing hcn integrated gene(s) is that the number of copies of the gene(s) to be integrated can easily be controlled. For example, more copies of the XR-XD-XK genes can be inserted into the fusion yeast 1400 chromosome if another selection marker, such as $Km^R$, is inserted into the 5S rDNA fragment (or the targeting sequence). Furthermore, the inventive methods for the development of hcn yeast integrants are also easier to accomplish than other reported approaches, wherein experimental conditions may have to be adjusted and controlled and the transformation process may have to be repeated before a stable strain could be obtained.

Thus, the applicants have improved upon the stability of prior recombinant xylose-fermenting yeasts, such as 1400 (pLNH32) and 1400 (pLNH33), and developed advantageously stable recombinant yeasts, for example 1400 (LNH-ST), that will not require the presence of selection pressure to maintain the cloned genes and are also as effective as or even more effective for cofermenting glucose and xylose than 1400 (pLNH32) and 1400 (pLNH33). Furthermore, the applicants have also developed a convenient method that has provided the facile hcn integration of exogenous gene(s) into the cellular chromosome, wherein the number of copies of the gene(s) to be integrated is also readily controllable.

Similar to 1400 (pLNH32) and 1400 (pLNH33), the preferred stable genetically engineered xylose-fermenting yeasts of the invention can also effectively coferment both glucose and xylose. This is because the XR, XD, and XK genes inserted into the chromosome of the new yeast hosts are all fused to intact 5' non-coding sequences from genes that can be efficiently expressed in yeast, encoding the production of high levels of enzymes, and also which are not inhibited by the presence of glucose in the medium. For example, the intact 5' non-coding DNA sequences that contain all the genetic elements for efficient expression of the glycolytic genes and for the production of high levels of glycolytic enzymes are suitable as replacements for the intact 5' non-coding sequences of XR, XD, and XK for these purposes.

The XR, XD, and XK cloned on PLNH-ST are from *Pichia stipitis* (XR and XD) and *Saccharomyces cerevisiae*. (XK). However they can be from any microorganisms as long as they can produce high levels of the respective enzymes after they have been fused to the proper 5' non-coding sequences containing effective promoters, ribosomal binding sites, etc. For example, these three genes are well known to occur in a wide variety of microorganisms and numerous XR, XD and XK genes have been identified and isolated. The particular source of these genes is thus not critical to the broad aspects of this invention; rather, any DNAs encoding proteins (enzymes) having xylose reductase activity (the ability to convert D-xylose to xylitol with NADPH and/or NADH as cofactor), xylitol dehydrogenase activity (the ability to convert xylitol to D-xylulose with $NAD^+$ and/or $NADP^+$ as cofactor), or xylulokinase activity (the ability to convert D-xylulose to D-xylulose-5-phosphate) will be suitable. These genes may be obtained as naturally-occurring genes, or may be modified, for example, by the addition, substitution or deletion of bases to or of the naturally-occurring gene, so long as the encoded protein still has XR, XD or XK activity. Similarly, the genes or portions thereof may be synthetically produced by known techniques, again so long as the resulting DNA encodes a protein exhibiting the desired XR, XD or XK activity.

As examples, suitable sources of XR and XD genes include xylose-utilizing yeasts such as *Candida shehatae, Pichia stipitis, Pachysolen tannophilus*, suitable sources of XK genes include the above-noted xylose-utilizing yeasts, as well a xylose non-utilizing yeasts such as those from the genus *Saccharomyces*, e.g. *S. cerevisiae*, the genus *Schizosaccharomyces*, e.g. *Schizosaccharomyces pombe*, and bacteria such as *Escherichia coli*, *Bacillus* species, *Streptomyces* species, etc. Genes of interest can be recovered from these sources utilizing conventional methodologies. For example, hybridization, complementation or PCR techniques can be employed for this purpose.

A wide variety of promoters will be suitable for use in the invention. Broadly speaking, yeast-compatible promoters capable of controlling transcription of the XR, XD or XK genes will be used. Such promoters are available from numerous known sources, including yeasts, bacteria, and other cell sources. Preferably, the promoters used in the invention will be efficient, non-glucose-inhibited promoters, which do not require xylose for induction. In this regard, an "efficient" promoter as used herein refers to a 5' flanking sequence which provides a high level of expression of the fused gene. Promoters having these characteristics are also widely available, and their use in the present invention, given the teachings herein, will be within the purview of the ordinarily skilled artisan, as will be the fusion of the promoters to the XR, XD and XK genes, the cloning of the promoter/gene fusion products into appropriate vectors and the use of the vectors to transform yeast. All of these manipulations can be performed using conventional genetic engineering techniques well known to the art and literature.

The yeast DNA replication origin, e.g. the ARS containing DNA fragment, can be obtained from yeast chromosomal DNA or from chromosomal DNA of other organisms, so long as the DNA fragment can function as an active replication origin to support autonomous replication of plasmid in the host chosen for hcn integration. DNA fragments which function as ARSs can readily be isolated by incorporating randomly-digested DNA fragments into an *E. coli* plasmid, followed by transformation of the desired host organism, e.g. a *Saccharomyces* yeast, with the resulting bank of plasmids, as reported in the literature (Stinchcomb et al., 1980; Ho et al., 1984).

Novel methods have been used to create the stable strains of the present invention. Nevertheless, there are several lines of evidence indicating that the cloned genes are not on a replicative plasmid and have been integrated into the host genome. For example, chromosomal DNA isolated from 1400 (LNH-ST) can be used as template for the isolation of the cloned genes, including the fusions containing both the 5s rDNA and the cloned gene sequences, by the polymerase chain reaction (PCR). Also, while few plasmids (pLNH-ST) can be recovered from 1400 (LNH-ST) via transformation of *E. coli* (Ward, 1990), under the same conditions, hundreds of pLNH32 or pLNH33 plasmids can be recovered from 1400 (pLNH32) and 1400 (pLNH33), respectively. Furthermore, the initial 1400 fusion yeast transformants containing high copy numbers of the replicative plasmid PLNH-ST are unstable (with respect to their capability to ferment xylose) but positive for penicillinase (enzyme encoded by $Ap^R$) test (Chevallier and Aigle, 1979). On the contrary, the final stable transformants, 1400 (LNH-ST), which retain their capability for fermenting xylose without the presence of selection, are found to be negative for penicillinase test. This is expected if the exogenous DNA is integrated at the site of 5S rDNA since $Ap^R$ is not part of the DNA fragment to be integrated into the host chromosome. It is also possible that some of the stable yeast transformants may contain exogenous genes integrated at the ARS sites of the yeast chromosome.

For purposes of promoting a further understanding of the present invention and its features and advantages, the following Examples are provided. It will be understood, however, that these Examples are illustrative, and not limiting, of the invention.

EXAMPLE 1

Synthesis of the 5S rDNA Fragment by PCR

For the synthesis of the 5S rDNA fragment by PCR (to serve as the yeast DNA sequence for targeting high-copy-number integration into the yeast chromosome), the following oligonucleotides were synthesized and used as the primers for PCR reactions according to the published 5S rDNA sequence (Valenzuela et al., 1977). In addition to the 5S rDNA sequence, additional nucleotides specifying the SalI restriction site were also added to the 5' terminal of primers to facilitate the cloning of the PCR synthesized 5S rDNA into an *E. coli* plasmid.

Oligonucleotide I: TTAGTCGACGTCCCTCCAAATG-TAAAATGG.

Oligonucleotide II: AATGTCGACGTAGAAGAGAGG-GAAATGGAG

Chromosomal DNA isolated from fusion yeast 1400 was used as the template for the PCR reaction. The PCR synthesized 5S rDNA fragment was first cloned into the *E. coli* pBluescript II KS(−) plasmid (Stratagene Cloning Systems, La Jolla, Calif.) at its SalI site. The resulting plasmid was designated as pKS-rDNA(5S).

EXAMPLE 2

Insertion of XhoI Site into Cloned 5S rDNA Sequence

The nucleotide sequence between −29 and -56 of the 5S rDNA sequence (Valenzuela et al., 1977) was modified by oligonucleotide-mediated site-specific mutagenesis (Kunkel, 1985; Kunkel et al., 1987). As a result, an XhoI restriction site was inserted at the specific site described above. The protocol provided by Bio-Rad Laboratories, Inc. for oligonucleotide-mediated site-specific mutagenesis was followed to accomplish this task, except that pKS plasmid was used rather than plasmid pTZ18U or pTZ19U. The resulting plasmid containing the mutated 5S rDNA was designated as pKS-5S rDNA (XhoI). The following oligonucleotide was used to carry out the site-specific mutagenesis: GAGGGCAGGCTCGAGA-CATGTTCAGTAGG.

EXAMPLE 3

Isolation of DNA Fragments from *S. Cerevisiae* DNA or Other DNA Functioning as ARS in Yeasts

Figure 12:
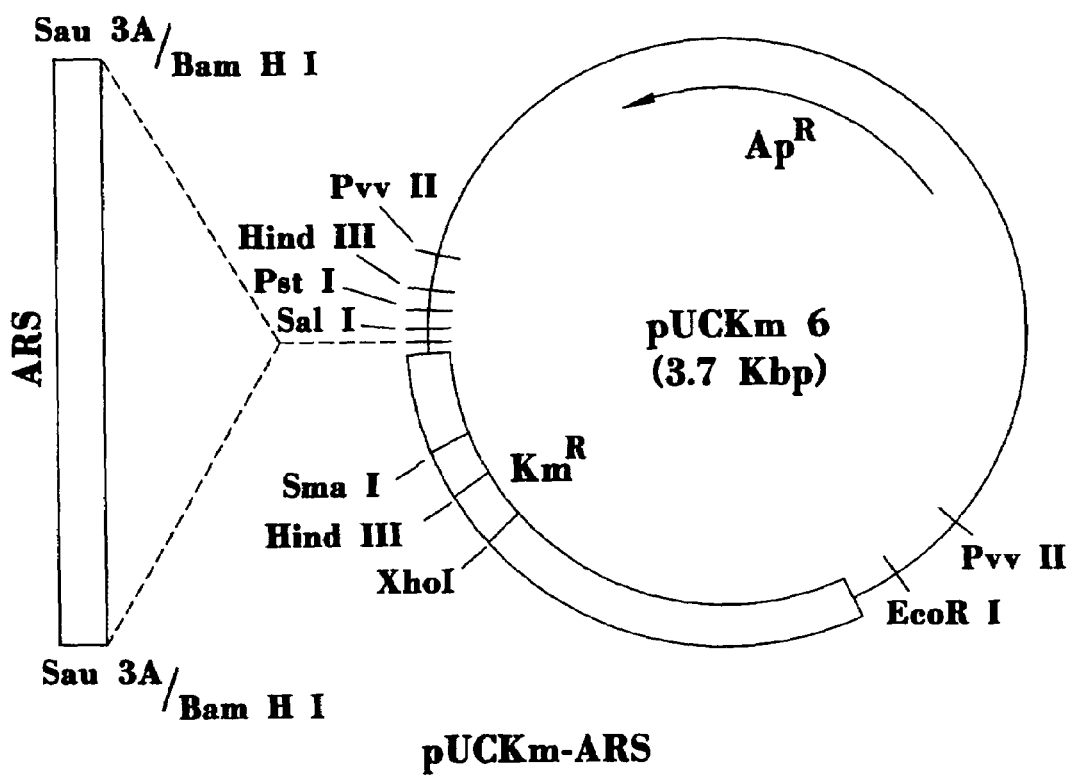
FIG. 12 shows the genes cloned in and the restriction map of a broad-host plasmid for the isolation of ARS containing DNA fragments from the chromosome DNA of *S. cerevisiae* and other yeasts.

*S. cerevisiae* DNA (or DNA from other yeasts or other organisms) was digested with Sau3A restriction enzyme and cloned into the Bam H1 site of pUCKm6 (FIG. 12) (Ho, et al., 1984). The resulting bank of plasmids was used to transform *S. cerevisiae*. Those transformants that were capable of growing on plates containing YEPD (1% yeast extract, 2% peptone, and 2% glucose) and 50 µg/ml geneticin and which were also positive for the penicillinase test (Chevallier and Algle, 1979) were selected. The plasmids from the selected true transformants were recovered by a procedure similar to that described by Ward (1990).

The yeast DNA fragments inserted in pUCKm6 (FIG. 12) and recovered from the yeast transformants should all contain a segment of DNA that can function as an ARS (autonomous replicating sequence) in *S. cerevisiae*, possibly in other yeasts as well. The DNA inserts were digested with various restriction enzymes and the resulting DNA fragments were re-inserted into pUCKm6. The latter plasmids were used to retransform *S. cerevisiae*. Any properly-sized restriction fragments that can make pUCKm6 function effectively as a yeast plasmid must contain an effective "ARS" and can be used to construct replicative/integrative vectors such as PLNH-ST for high-copy-number integration of exogenous gene(s) into the chromosomes of *S. cerevisiae*. These restriction fragments are also likely to function as ARS's in other yeasts, and are suitable for the construction of replicative/integrative plasmids for other yeasts.

EXAMPLE 4

Removal of the XhoI Restriction Site from the Geneticin (Kanamycin) Resistance Gene, $KM^R$ The geneticin (kanamycin) resistance gene, $Km^R$, from Tn 903 (A. Oka et al., 1981) and the 5S rDNA fragment described in Example 1 are part of the plasmid designed for the integration of multiple copies of exogenous genes into the yeast chromosome. However, $Km^R$ contains an XhoI site in its coding sequence. This is in conflict with the fact that an XhoI site has been engineered into the center of the cloned 5S rDNA sequence to be used for inserting exogenous genes such as XR, XD, and XK into the plasmid for integration. Thus, it is necessary to remove the XhoI site from $Km^R$. This can be accomplished by a number of different approaches. The applicants chose to use site-specific mutagenesis by the overlap extension PCR technique (S, N. Ho, et al., 1989) to remove the XhoI site from $Km^R$ without changing its amino acid coding sequence and without affecting the catalytic activity of the enzyme encoded by the gene. The $Km^R$ gene cloned in pUCKm6 (FIG. 12) was converted to $Km^R(-Xho)$ as described above.

The four oligonucleotides used to accomplish this task are listed below.

Oligonucleotide I: GGCCAGTGAATTCTCGAGCAGTTG-GTG

Oligonucleotide II: TGGAATTTAATCGCGGCCCCTAG-CAAGACG

Oligonucleotide III: TTACGCCAAGCTTGGCTGC

Oligonucleotide IV: TTCAACGGGAAACGTCT-TGCTAGGGGCCGC pUCKm6 (FIG. 12) is a derivative of pUC9. Part of Oligo I and the entire Oligo III are synthesized according to the sequence of the polylinker region of pUC9 (Sambrook, et al. 1989).

The above-described genetic manipulation of pUCKm6 not only resulted in the deletion of the XhoI restriction site from the coding region of $Km^R$ but also inserted an XhoI restriction site between the $Km^R$ coding sequence and the EcoRI site of pUCKm6. The resulting plasmid was designated as pUCKm(-XhoI)(+XhoI). The addition of an XhoI site downstream to the $Km^R$ coding sequence is to facilitate the insertion of the 5S rDNA fragment described in Example 1 into the newly developed plasmid pUCKm(-Xho)(+Xho).

EXAMPLE 5

Construction of Plasmid pLNH-ST

The plasmid pUCKm(-XhoI)(+XhoI) described in Example 4 was used for the construction of pLNH-ST, shown in FIG. 9. First, the SalI fragment containing the 5S rDNA (XhoI) was isolated from pKS-5S rDNA(XhoI) and inserted at the XhoI site of pUCKm(-XhoI)(+XhoI). The resulting plasmid was designated as pUCKm-rDNA(5S). To the latter plasmid, an EcoRI fragment containing an effective ARS isolated from *S. cerevisiae* (according to the procedure described in Example 3) was inserted into the EcoRI site of pUCKm-5S rDNA, and the resulting plasmid was designated as pUCKm-5S rDNA-ARS. To the latter plasmid, the XhoI fragment from pKS(-)-KK-AR-KD-3 containing the cloned XR, XD, and XK fused to yeast alcohol dehydrogenase promoter (XR), and pyruvate kinase promoter (for both XD & XK), were inserted into the XhoI site located at the center of the cloned 5S rDNA sequence. The resulting plasmid, pUCKm-rDNA(5S)(KDR)-ARS, also designated pLNH-ST, shown in FIG. 9.

EXAMPLE 6

Transformation of Fusion Yeast 1400 with pLNH-ST and Selection of Stable Transformants 1400 (LNH-ST)

pLNH-ST was used to transform fusion strain 1400 by electroporation under the conditions used for transformation of strain 1400 by plasmids pLNH32 and pLNH33 (International Publication No. 95/13362, May 18, 1995, publishing International Application No. PCT/US94/12861, filed Nov. 8, 1994). Briefly, fifty ml yeast cells, grown to early log phase (Klett Unit (KU) 140-190), were centrifuged to remove the medium, washed twice with cold water, once with cold 1 M sorbitol, and resuspended in 200 µl 1 M sorbitol. Sixty µl of the cells were transferred into a 4 ml presterilized plastic tube (with cap) and to which 1 µg plasmid DNA was added. Fifty µl of the resulting cells and plasmid mixture were pipetted into a precooled gene pulser cuvette with a 0.2 cm electrode gap and the content in the cuvette was subjected to pulse by the gene pulser with a pulse controller (BioRad) at 2.0 KV, 25 µF, 200 ohms.

Immediately, 0.50 ml YEPD was added to the cuvette. The content of the cuvette was transferred to a new 4 ml sterilized plastic tube and incubated at 30° C. for 1 hr. 100 µl of the cells were plated on agar plates containing YEPD and 40 µg/ml G418 (geneticin). Fast growing colonies were selected and replicated on another plate containing the same medium. The selected colonies were subjected to the ampicillin test (Chevallier and Aigle, 1979) until a positive one was identified. The above-described electroporation procedure is based on that reported by Becker and Guarente (1971).

Once a transformant had been positively identified by the penicillinase test, it was maintained on a YEPX (1% yeast extract, 2% peptone, 2% xylose) plate. Initially, the transformants were very unstable. They lost their xylose fermenting capability if cultured in YEPD medium over 20 generations. However, by continuing to culture the transformants to stationary phase on YEPX plates, and repeatedly transferring them to fresh YEPX plates, the transformants gradually became stable with regard to their capability to ferment xylose. Once stable, the transformants could be cultured in non-selective medium for several hundred or more generations and were still capable of co-fermenting both glucose and xylose, as demonstrated in Example 8.

EXAMPLE 7

Co-Fermentation of Glucose and Xylose with 1400 (LNH-ST)

A mixture of glucose and xylose (approximately 10% glucose and 5% xylose) was fermented by strain 1400 (LNH-ST) under the conditions described below. The seed cultures of 1400 and 1400 (LNH-ST) were cultured aerobically in liquid YEPD medium until mid-log phase (between 400-450 Klett Units (KU)) and stored at 4° C. New seed cultures were prepared once a month by transferring 2 ml of the culture to 50 ml of fresh YEPD and cultured as described above. 2 ml of the seed cultures of 1400 (LNH-ST) were inoculated into 100 ml of YEPD medium in a 300 ml Erlenmeyer flask equipped with a side-arm which allowed direct monitoring of the growth of the yeast cultures by the Klett colorimeter. The culture was incubated in a shaker at 30° C. and 200 rpm aerobically.

When the cell density reached mid-log phase (400-450 KU), 20 ml (50%) glucose and 10 ml (50%) xylose were added to the flask. After thorough mixing, 1 ml of the culture mixture was removed from the flask to serve as the zero sample. The flask was then sealed with Saran wrap to allow fermentation to be carried out anaerobically. One ml samples of the fermentation broth were removed at proper intervals (every 6 hrs.) to serve as samples for measuring glucose, xylose, xylitol, and glycerol contents of the broth during fermentation by HPLC as described in Example 9. The results, shown in FIG. 11, demonstrate that the genetically engineered yeast 1400 (LNH-ST) can co-ferment most of the 10% glucose and 5% xylose to ethanol in 30 hrs. The fermentation was carried out under normal conditions, without requiring special medium or pH, and also without requiring growth of yeast to high cell density. Thus, the genetically engineered 1400 (LNH-ST) can effectively co-ferment high concentrations of both glucose and xylose to ethanol with very little xylitol produced as a by-product. In comparison to the recombinant *Saccharomyces* 1400 (pLNH32) and 1400 (pLNH33) shown in FIGS. 2 and 3, 1400 (LNH-ST) co-fermented both glucose and xylose somewhat better than the two previously developed yeasts.

EXAMPLE 8

Comparison of the Stable Strain 1400 (LNH-ST) with 1400 (LNH32) and 1400 (LNH33) in Co-Fermenting Glucose and Xylose After Culture in Non-Selective Medium for 4, 20, and 40 Generations As described in Example 7, 2 ml each of the seed cultures of 1400 (LNH-ST), 1400 (LNH32), and 1400 (LNH33) were inoculated into 50 ml YEPD in separate 250 ml Erlenmeyer flasks equipped with side-arms. After the cells were cultured to 400-450 KU, 2 ml of the fresh culture from each flask were transferred to a new flask. This process was repeated 10 times for 1400 (LNH-ST) and 5 times for 1400 (LNH32) and 1400 (LNH33). The 1400 (LNH-ST) cultures that were cultured for 4, 20, and 40 generations in non-selective medium (each transfer being considered as four generations cultured in non-selective medium) were used to co-ferment glucose and xylose under similar conditions described in Example 7. The fermentation samples were taken and analyzed identically as described in Example 7. Similarly, the 1400 (LNH32) and 1400 (LNH33) cultures that were cultured for 4 and 20 generations in non-selective medium were used to co-ferment glucose and xylose. Samples were again taken at proper intervals after fermentation was initiated for analysis by HPLC and compared in FIGS. 4 to 6. These results clearly demonstrate that 1400 (LNH-ST) is far more stable than 1400 (LNH32) and 1400 (LNH33) in maintaining its xylose fermenting capability after being cultured in non-selective medium for more than 40 generations.

EXAMPLE 9

HPLC Analysis of Fermentation Samples

The samples containing the fermentation broth (0.6 ml to 1.0 ml) removed from the cultures were kept in 1.5 ml Eppendorf tubes. The cells and other residues were removed by centrifugation in microfuge (topspeed) for 10 min. The supernatant was diluted 10 fold. The resulting diluted samples were analyzed for its ethanol, glucose, xylose, xylitol, and glycerol contents by high performance liquid chromatography (HPLC), using a Hitachi system according to the following conditions.

Column: BioRad HPX-87H
Mobile Phase: 0.005 M $H_2SO_4$
Flow Rate: 0.8 ml/min.
Detection: RI detector
Temperature: 60° C.
Injection Volume: 20 μl

EXAMPLE 10

Genetic Characterization of Chromosomal DNA from the Stable Transformants 1400 (LNH-ST)

Figure 9B:
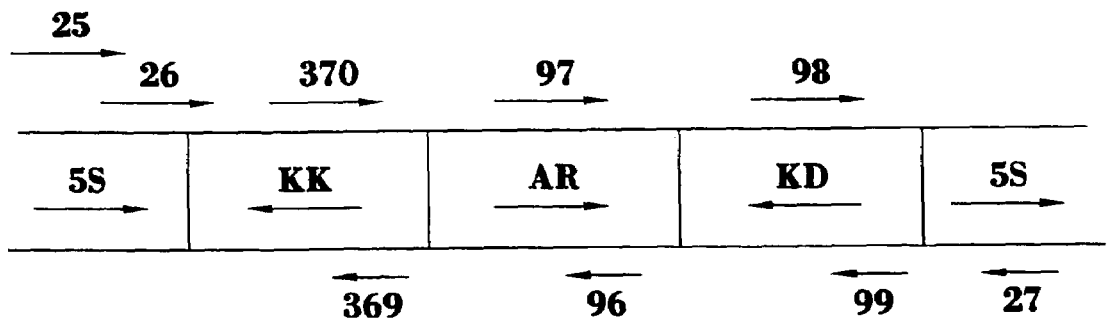
FIG. 9B shows the genetic map (the order and orientation) of genes (5S rDNA, KK, AR, and KD) cloned in pLNH-ST. The oligonucleotides (for example, Oligo 25, Oligo 26, etc.) that are above or below the gene map are the primers used to characterize the order and orientation of the cloned genes by PCR.
Figure 10:
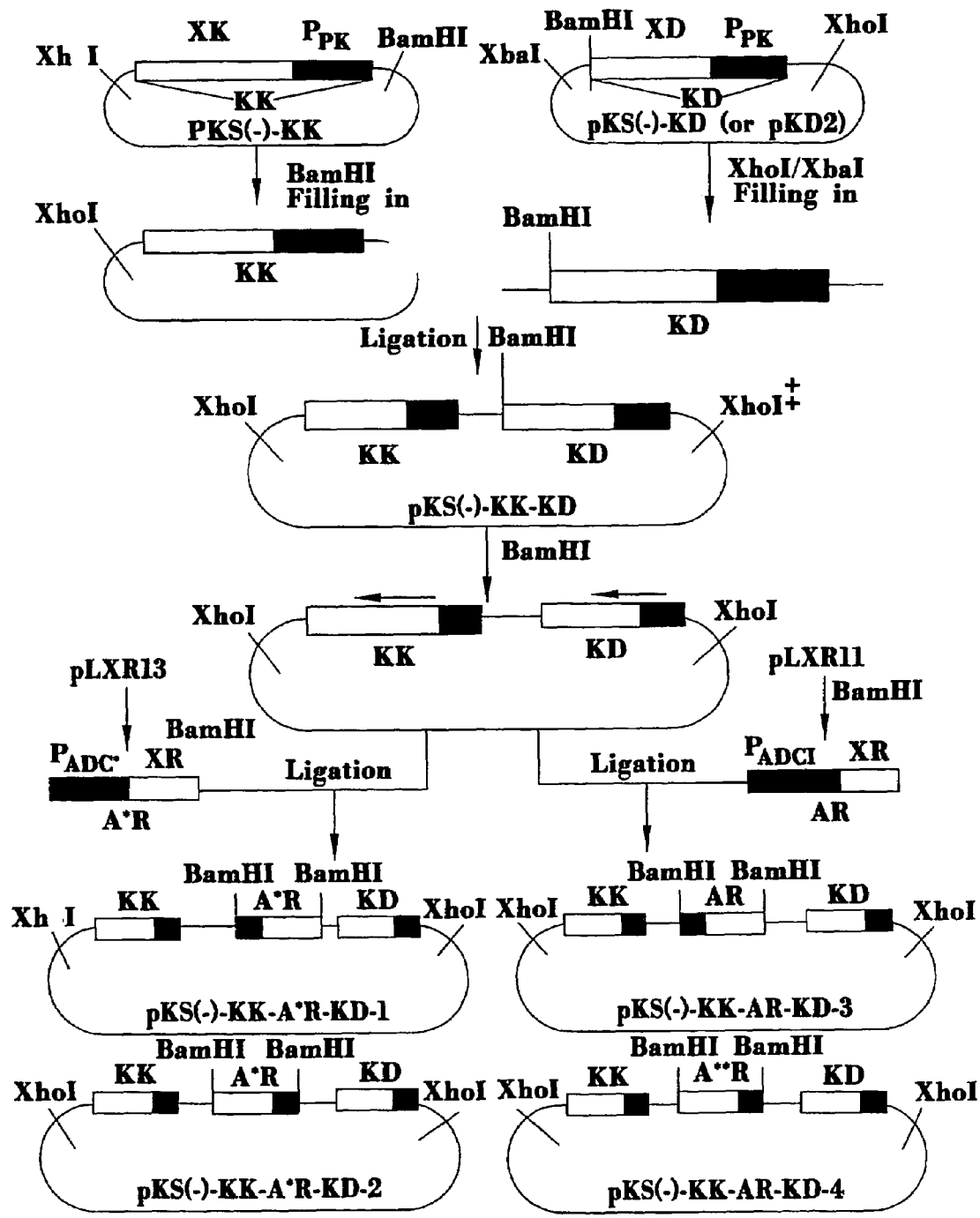
FIG. 10 is a schematic diagram outlining the construction of pBluescript II KS(-) containing the cloned XR, XD, XK genes: four such plasmids were constructed. The KK-AR-KD fragment cloned in pKS(-)-KK-AR-KD-3 was chosen to be cloned in pUCKm-rDNA(5S)-ARS for the construction of pUCKm-rDNA(5S)(KRD)-ARS, also designated as pLNH-ST.

Based on the restriction and PCR analysis, the genetic map (the order and orientation) of the cloned genes, KK, AR, KD, and 5S rDNA present in pLNH-ST, have been determined as shown in FIG. 9B. Experiments have been designed to determine whether these genes (KK, AR, and KD) have been integrated into the loci of the 5S rDNA. If these genes have been integrated into the yeast chromosome at the loci of the 5S rDNA as anticipated, the correct size of DNA fragments containing the following combination of partial or intact genes such as 5S rDNA-KK; 5S rDNA-KD; KK-AR, and AR-KD should have been obtained by using 1400 (LNH-ST) chromosomal DNA as the template and the oligonucleotides indicated on the genetic map (FIG. 9B) as the primers to carry out DNA synthesis by PCR. If these genes have not been integrated into the yeast chromosome, no such combination of genes or gene fragments should have been obtained by the above described experiments. If these genes have been integrated elsewhere in the yeast chromosome rather than at the loci of 5S rDNA, some of the above described combination of genes or gene fragments should be obtained from the above described experiments, but not those containing the 5S rDNA fragment; such as 5S rDNA-KK and 5S rDNA-KD. For carrying out the above described experiments, chromosomal DNA was isolated from 1400 (LNH-ST), using the protocol provided by Qiagen, Chatsworth, Calif. Positive results were obtained from PCR synthesis by using the following pairs of primers (see FIG. 9): Oligo 25 and Oligo 369; Oligo 26 and Oligo 369; Oligo 370 and Oligo 96; Oligo 97 and Oligo 99; Oligo 982 and Oligo 27. Thus, based on these analyses, the DNA fragment containing KK-AR-KD seems indeed being integrated in the 1400 yeast chromosome at its 5S rDNA loci.

REFERENCES

The following publications are indicative of the level of skill possessed by those in the art and are each hereby incorporated by reference as if individually incorporated by reference and fully set forth.
1. Chan, C. S. M., and B.-K. Tye (1980), "Autonomously replicating sequences in *Saccharomyces cerevisiae*," *Proc. Natl. Acad. Sc.*, 77(11), 6329-6333.
2. Cregg, J. M., K. J. Barringer, A. Y. Hessler, and K. R. Madden (1985), "*Pichia pastoris* as a Host System for Transformations," *Molecular and Cellular Biology*, 5, 3376-3385.
3. D'Amore, T., G. Celotto, I. Russell, and G. G. Stewart (1989), "Selection and Optimization of Yeast Suitable for Ethanol Production at 40°" *Enz. Microbial. Technol.* 11, 411-416.
4. D'Amore, T., J. P. Chandra, I. Russell, and G. G, Stewart (1990), "A Study of ethanol Tolerance in Yeast" *Critical Reviews in Biotechnology* 9, 287-304.
5. Ho, N. W. Y., and Tsao, G. T., "Recombinant Yeasts capable of Effective Fermentation of both glucose and Xylose," International Publication No. 95/13362, May 18, 1995, publishing International Application No. PCT/US94/12861, filed Nov. 8, 1994.
6. Kudla, B., and A. Nicolas (1992), "A multisite integrative cassette for the yeast *Saccharomyces cerevisiae*," *Gene.* 119, 49-56.
7. Kurtz, M. B., M. W. Cortelyou, and D. R. Kirsch (1986), "Integrative Transformation of *Candida albicans*, Using a Cloned *Candida ADE2 Gene*," *Molecular and Cellular Biology*, 142-149.
8. Lopes, T. S., J. Klootwijk, A. E. Veenstra, P. C. van der Aar, H. van Heerikhuizen, H. A. Raué, and R. J. Planta (1989), "High-copy-number integration into the ribosomal DNA of *Saccharomyces cerevisiae*: a new vector for high-level expression," *Elsevier Science Publishers*, 79, 199-206.
9. Lopes, T. S., Gert-Jan A. J. Hakkaart, B. L. Koerts, H. A. Raué, and R. J. Planta (1991), "Mechanism of high-copy-number integration of pMIRY-type vectors into the ribosomal DNA of *Saccharomyces cerevisiae*," *Elsevier Science Publishers*, 105, 83-90.
10. Orr-Weaver, T. L., J. W. Szostak, and R. J. Rothstein (1981), "Yeast transformation: A model system for the study of recombination," *Proc. Natl. Acad. Sci.*, 78(10), 6354-6358.
11. Orr-Weaver, T. L., and J. W. Szostak (1983), "Multiple, Tandem Plasmid Integration in *Saccharomyces cerevisiae*," *Molecular and Cellular Biology*, 3(4), 747-749.
12. Romanos, M. A., C. A. Scorer, and J. J. Clare (1992), "Foreign Gene Expression in Yeast: a Review," *John Wiley & Sons Ltd.*, 8, 423-488.
13. Rossolini, M., M. L. Riccio, E. Gallo, and C. L. Galeotti (1992), "*Saccharomyces lactis* rDNA as a target for multiple integration by homologous recombination," *Elsevier Science Publishers*, 75-81.
14. Rothstein, R. J. (1981), "One-Step Gene Disruption in Yeast," *Methods in Enzymology*, 101, 202-211.
15. Rothstein, R. J. (1991), "Targeting, Disruption, Replacement, and Allele Rescue: Integrative DNA Transformation in Yeast," *Methods in Enzymology*, 194, 281-301.
16. Sakai, A., Y. Shimizu, and F. Hishinuma (1990), "Integration of heterologous genes into the chromosome of *Saccharomyces cerevisiae* using a delta sequence of yeast retrotransposen Ty," *Appl. Microbiol. Biotechnol.*, 33, 302-306.
17. Sakai, A., F. Ozawa, T. Higashizaki, Y. Shimizu, and F. Hishinuma (1991), "Enhanced Secretion of Human Nerve Growth Factor from *Saccharomyces cerevisiae* Using an Advanced d-Integration System," *Bio/Technology*, 9, 1382-1385.
18. Stinchcomb, D. T., M. Thomas, J. Kelly, E. Selker, and R. W. Davis (1980), "Eukaryotic DNA segments capable of autonomous replication in yeast," *Proc. Natl. Acad. Sci.*, 77(8), 4559-4563.
19. Struhl, K., D. T. Stinchcomb, S. Scherer, and R. W. Davis (1979), "High-frequency transformation of yeast: Autonomous replication of hybrid DNA molecules," *Proc. Natl. Acad. Sci.*, 76(3), 1035-1039.
20. Szostak, J. W., and R. Wu (1979), "Insertion of a Genetic Market into the Ribosomal DNA of Yeast," *Plasmid*, 2, 536-554.
21. Valenzuela, P., G. I. Bell, A. Venegas, E. T. Sewell, F. R. Masiarz, L. J. DeGennaro, G. Weinberg, and W. J. Rutter (1977), "Ribosomal RNA genes of *Saccharomyces cerevisiae* II. Physical map and nucleotide sequence of the 5 S ribosomal RNA gene and adjacent intergenic Regions," *The Journal of Biological Chemistry*, 252(22), 8126-8135.
22. Chevalier, M. R. and M. Algle (1979), "Qualitative detection of penicillinnase produced by yeast strains carrying chimeric yeast—Coli plasmid", *Febs Letters*, 108.179-180.
23. Ho, N. W. Y., H. C. Gao, J. J. Huang, P. E. Stevis, S. F. Chang (1984), "Development of a cloning system for *Candida* species" *Biotechnol. Bioengineering Symp. No. 14*, 295-301.
24. Ward, A. C. (1990), "Single-step purification of shuttle vectors from yeast for high frequency back-transformation into *E. coli*", *Nucleic Acids Research*, 18, 5319.
25. Becker, D. M. and L. Guavente, (1991), "High-efficiency transformation of yeast by electroporation," Methods in Enzymology 194, 182-187.
26. Ho, S., N., Hunt, H. D., Horton, R. M., Pullen, J. K., and Pease, L. R., (1989), "Site-directed mutagenesis by overlap extension using the polymerase chain reaction, *Gene*, 77, 51.
27. Kunkel, T. A., (1985), *Proc. Natl. Acad. Sci. USA*, 82, 488.
28. Kunkel, T. A., Roberts, J. D. and Zakour, R. A., (1987), *Meth. Enzymol.*, 154, 367.
29. Sambrook, J., E. F. Fritsch, and T. Maniatis, (1989), "Molecular Cloning," published by Cold Spring Harbor Lab. Press, 4.10-4.11.

What is claimed is:

1. A method of integrating multiple copies of exogenous DNA into reiterated chromosomal DNA of cells, comprising:
   (a) transforming the cells with a replicative and integrative plasmid comprising an autonomous replicating sequence, exogenous DNA, and a first selection marker; and
   (b) repeatedly replicating the cells from step (a) to produce a number of generations of progeny cells while selecting for cells which include the selection marker, promoting the retention of the replicative and integrative plasmid in subsequent generations of the progeny cells to produce progeny cells having multiple integrated copies of the exogenous DNA, and wherein the method further includes the step of repeatedly replicating the progeny cells to produce a number of generations of progeny cells in the absence of selection for cells which include the selection marker, so as to promote the loss of the plasmid in subsequent generations of progeny cells and recovering the cells each containing multiple copies of the exogenous DNA integrated into its chromosomal DNA, and wherein the cells are yeast cells and the exogenous DNA includes genes encoding xylose reductase, xylitol dehydrogenase, and xylulokinase, which also serve as the first selection marker.

2. A plasmid vector comprising a functional yeast autonomous replicating sequence and exogenous DNA including genes encoding xylose reductase, xylitol homologous to a reiterated DNA sequence of a target yeast cell, the plasmid vector for use in integrating the exogenous DNA sequence into chromosomal DNA of the target yeast to form stable integrants which ferment xylose to ethanol.

3. The method of claim 1, wherein the plasmid also includes a second selection marker for selecting cells which include the plasmid.

* * * * *